(12) United States Patent
Harada et al.

(10) Patent No.: US 10,757,357 B2
(45) Date of Patent: Aug. 25, 2020

(54) IMAGING ELEMENT, IMAGING DEVICE, AND ENDOSCOPE

(71) Applicant: OLYMPUS CORPORATION, Tokyo (JP)

(72) Inventors: Yasunari Harada, Ebina (JP); Shuzo Hiraide, Tokyo (JP); Masato Osawa, Hachioji (JP); Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/442,666

(22) Filed: Jun. 17, 2019

(65) Prior Publication Data

US 2019/0373197 A1    Dec. 5, 2019

Related U.S. Application Data

(63) Continuation of application No. PCT/JP2017/032168, filed on Sep. 6, 2017.

(30) Foreign Application Priority Data

Dec. 21, 2016 (JP) ................. 2016-247963

(51) Int. Cl.
*H04N 5/378* (2011.01)
*A61B 1/00* (2006.01)
(Continued)

(52) U.S. Cl.
CPC ......... *H04N 5/378* (2013.01); *A61B 1/00009* (2013.01); *A61B 1/00172* (2013.01); *A61B 1/045* (2013.01); *H04N 5/3651* (2013.01)

(58) Field of Classification Search
CPC ...... H04N 5/378; H04N 5/3651; H04N 5/374; H04N 5/3575; H04N 5/365; H04N 5/3658;
(Continued)

(56) References Cited

U.S. PATENT DOCUMENTS

2012/0273655 A1* 11/2012 Ise .................. H04N 5/361
                                                250/208.1
2016/0295142 A1    10/2016 Yoshida
(Continued)

FOREIGN PATENT DOCUMENTS

JP    H08079028 A    3/1996
JP    2010016782 A    1/2010
(Continued)

OTHER PUBLICATIONS

International Search Report dated Nov. 21, 2017 issued in PCT/JP2017/032168.

*Primary Examiner* — Yogesh K Aggarwal
(74) *Attorney, Agent, or Firm* — Scully, Scott, Murphy & Presser, P.C.

(57) ABSTRACT

An imaging element includes: a plurality of pixels where each pixel is configured to generate an imaging signal; a noise eliminating circuit configured to eliminate a noise component included in the imaging signal; a plurality of column source follower buffers where each column source follower buffer is configured to amplify the imaging signal from which the noise component has been eliminated by the noise eliminating circuit, and output the amplified signal; a horizontal scanning circuit configured to sequentially select the column source follower buffer and output the imaging signal; and a buffer circuit which is connected with the column source follower buffer sequentially selected by the horizontal scanning circuit to form a voltage follower circuit, the buffer circuit being configured to perform imped- (Continued)

ance conversion on a voltage of the imaging signal output from the column source follower buffer, and output the converted signal to an outside.

9 Claims, 18 Drawing Sheets

(51) Int. Cl.
*A61B 1/045* (2006.01)
*H04N 5/365* (2011.01)

(58) Field of Classification Search
CPC ...... H04N 5/369; H04N 5/3698; H04N 5/363; H04N 5/3745; H04N 5/37452; H04N 5/357–5/3675; A61B 1/00009; A61B 1/00172; A61B 1/045; A61B 1/05; A61B 1/00006; G02B 23/24

USPC ........ 348/241–251, 300, 308; 382/274, 275; 257/443

See application file for complete search history.

(56) References Cited

U.S. PATENT DOCUMENTS

| | | | |
|---|---|---|---|
| 2016/0373666 A1* | 12/2016 | Ono | ........................ H04N 5/357 |
| 2017/0041016 A1 | 2/2017 | Harada | |
| 2017/0339327 A1* | 11/2017 | Koshkin | .............. H04N 5/2253 |

FOREIGN PATENT DOCUMENTS

| | | |
|---|---|---|
| JP | 2015216446 A | 12/2015 |
| JP | 2016192594 A | 11/2016 |
| WO | 2016052173 A1 | 4/2016 |

* cited by examiner

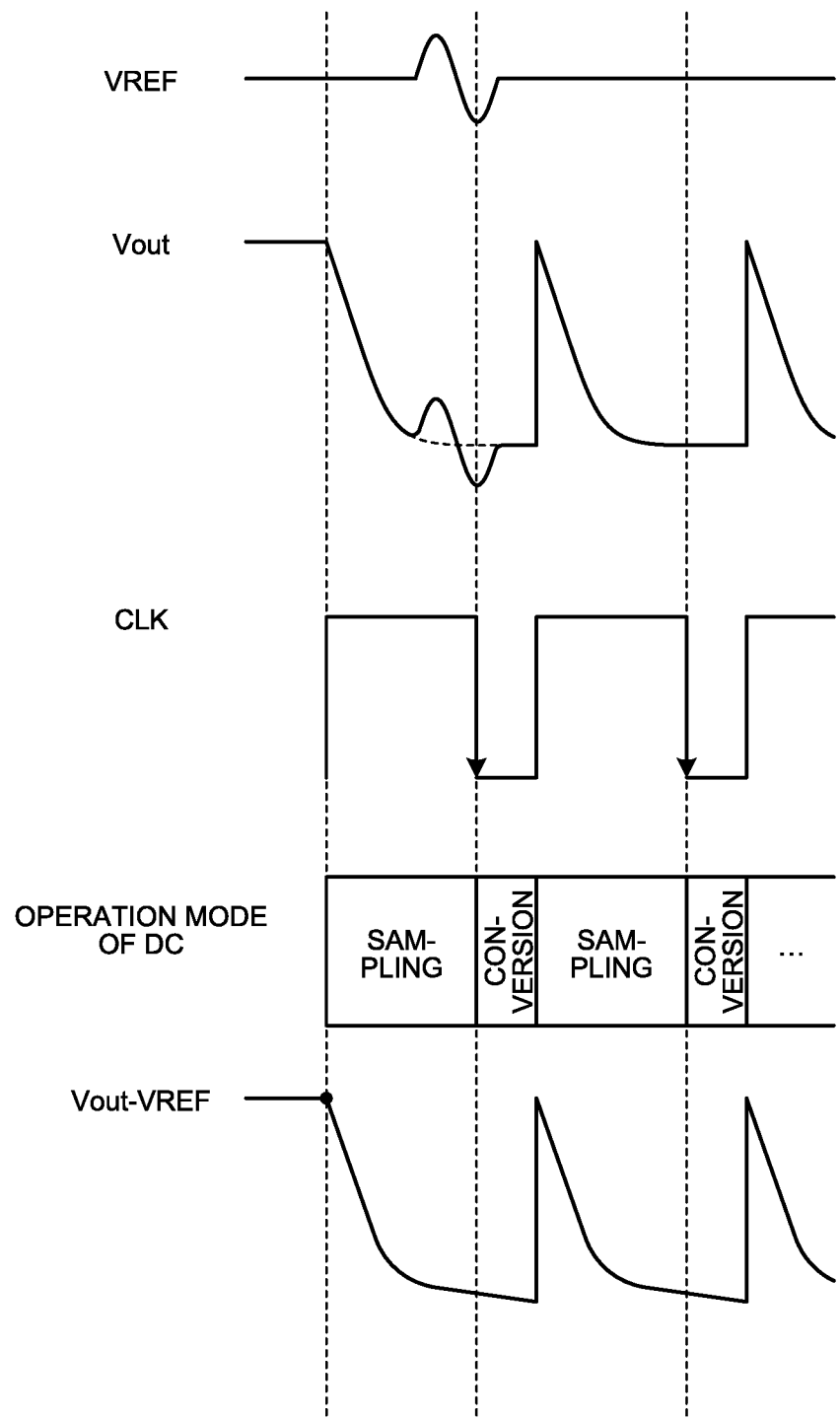

IMAGING ELEMENT, IMAGING DEVICE, AND ENDOSCOPE

CROSS-REFERENCE TO RELATED APPLICATION

This application is a continuation of PCT international application Ser. No. PCT/JP2017/032168, filed on Sep. 6, 2017 which designates the United States, incorporated herein by reference, and which claims the benefit of priority from Japanese Patent Applications No. 2016-247963, filed on Dec. 21, 2016, incorporated herein by reference.

BACKGROUND

The present disclosure relates to an imaging element, an imaging device, and an endoscope which are introduced into a subject and generate image data of the subject.

There is known a technique for amplifying an imaging signal from a pixel and outputting the amplified signal to an A/D converter using a source follower circuit in a readout circuit provided for each column of pixels of an imaging element of a complementary metal oxide semiconductor (CMOS) image sensor (see Japanese Laid-open Patent Publication No. 2010-16782).

SUMMARY

An imaging element according to the disclosure includes: a plurality of pixels which are arranged in a two-dimensional matrix, each pixel being configured to receive light from an outside and perform photoelectric conversion to generate an imaging signal; a noise eliminating circuit which is provided for each of columns in an arrangement of the plurality of pixels, the noise eliminating circuit being configured to eliminate a noise component included in the imaging signal; a plurality of column source follower buffers which are provided, respectively, for the columns in the arrangement of the plurality of pixels, each column source follower buffer being configured to amplify the imaging signal from which the noise component has been eliminated by the noise eliminating circuit, and output the amplified signal; a horizontal scanning circuit configured to sequentially select the column source follower buffer and output the imaging signal; and a buffer circuit which is connected with the column source follower buffer sequentially selected by the horizontal scanning circuit to form a voltage follower circuit, the buffer circuit being configured to perform impedance conversion on a voltage of the imaging signal output from the column source follower buffer, and output the converted signal to the outside. The buffer circuit comprises: a first constant current source configured to read the imaging signal from which the noise component has been eliminated by the noise eliminating circuit; a first transistor which includes a source terminal connected to the column source follower buffer and a gate terminal connected to a signal line configured to transmit the imaging signal to the outside; a second transistor which includes a source terminal connected to ground and a drain terminal connected to a drain terminal of the first transistor and the signal line; a third transistor which includes a source terminal connected to the ground; and a second constant current source which is connected to a drain terminal of the third transistor, a gate terminal of the third transistor, and a gate terminal of the second transistor.

An imaging device according to the disclosure includes: the imaging element; and an optical system configured to form a subject image on a light receiving surface of the imaging element.

An endoscope according to the disclosure includes: the imaging device; and an insertion portion which is insertable into a subject and is provided with the imaging device at a distal end portion.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 16B is a schematic diagram enlarging a part of a timing chart of a region R2 of FIG. 16A;

DETAILED DESCRIPTION

Hereinafter, a description will be given regarding modes (hereinafter, referred to as "embodiments") for implementing an endoscopic system provided with an endoscope including an imaging device at a distal end portion of an insertion portion to be inserted into a subject. In addition, the present disclosure is not limited to the embodiments. Further, the same parts are denoted by the same reference signs when the drawings are described. In addition, it is necessary to note that the drawings are schematic, and a relation between a thickness and a width of each member, each ratio of the members, and the like are different from the actual ones. In addition, portions that have different sizes and ratios one another may be included among the drawings.

First Embodiment

Configuration of Endoscopic System

Figure 1:
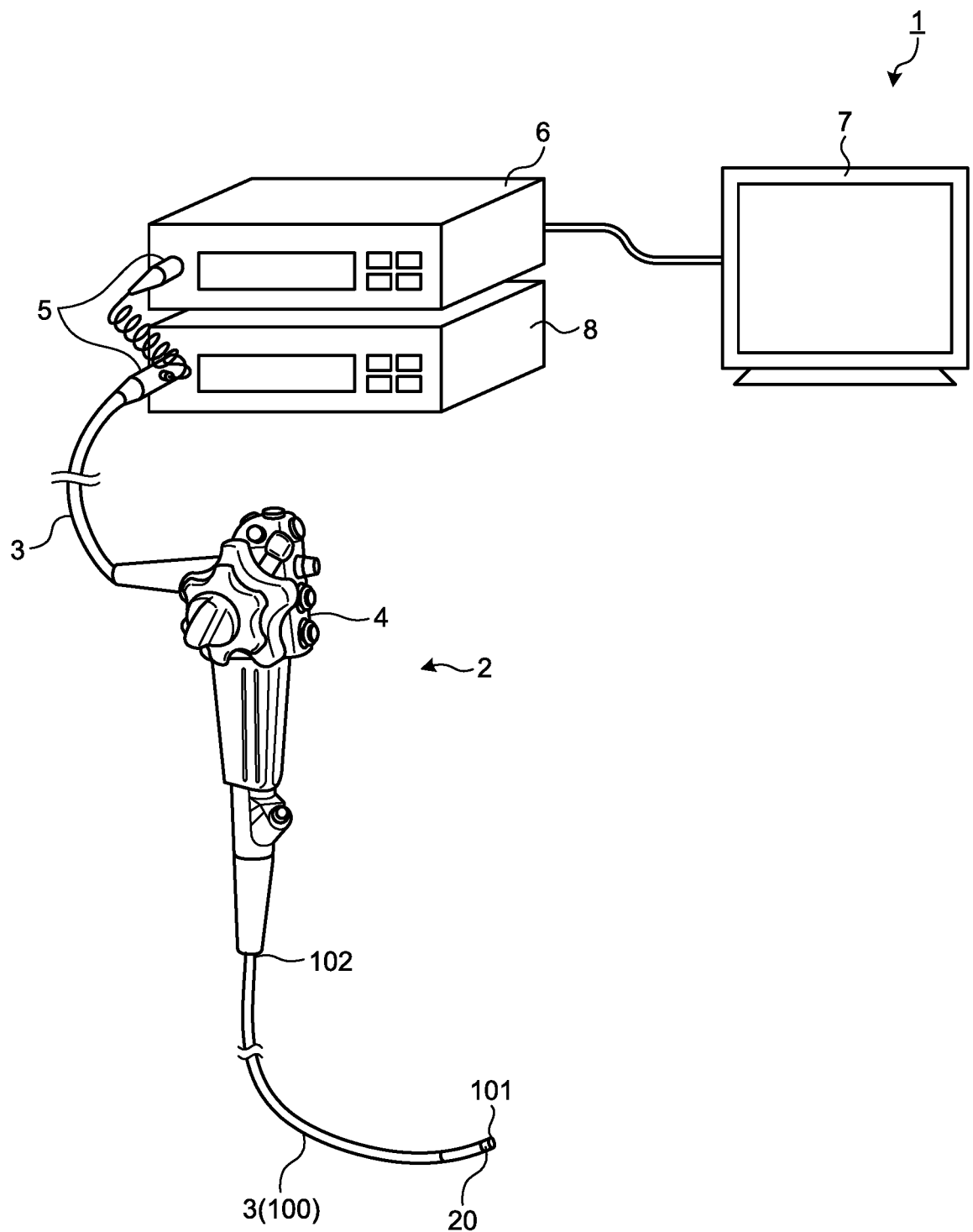
FIG. 1 is a schematic view illustrating an overall configuration of an endoscopic system according to a first embodiment of the disclosure.

FIG. 1 is a schematic view illustrating an overall configuration of an endoscopic system according to a first embodiment of the disclosure; An endoscopic system 1 illustrated in FIG. 1 is provided with an endoscope 2, a transmission cable 3, a connector unit 5, a processor 6, a display device 7, and a light source device 8.

The endoscope 2 captures the inside of a body of a subject by inserting an insertion portion 100, which is a part of the transmission cable 3, into a body cavity of the subject, and outputs an imaging signal to the processor 6. In addition, an endoscope 2 is provided with an imaging device 20 that captures the inside of a body of a subject to generate an imaging signal on one end side of a transmission cable 3 on a side of a distal end portion 101 of the insertion portion 100 to be inserted into a body cavity of the subject. Furthermore, the endoscope 2 is provided with an operating unit 4 that receives various operations on the endoscope 2 on a side of a proximal end portion 102 of the insertion portion 100. The imaging signal of an in-vivo image captured by the imaging device 20 is output to the connector unit 5 via the transmission cable 3 having a length of a few meters, for example.

The transmission cable 3 connects the endoscope 2 with a connector unit 5 and also connects the endoscope 2 with a processor 6 and a light source device 8. In addition, the transmission cable 3 transmits the imaging signal generated by the imaging device 20 to the connector unit 5. The transmission cable 3 is configured using a cable, an optical fiber, or the like.

The connector unit 5 is connected to the endoscope 2, the processor 6, and the light source device 8, performs predetermined signal processing on the imaging signal output from the connected endoscope 2, and outputs the processed signal to the processor 6.

The processor 6 performs predetermined image processing on the imaging signal input from the connector unit 5 and outputs the processed signal to a display device 7. In addition, the processor 6 comprehensively controls the entire endoscopic system 1. For example, the processor 6 performs control to switch illumination light emitted from the light source device 8 or to switch an imaging mode of the endoscope 2.

The display device 7 displays an image that corresponds to the imaging signal that has been subjected to the image processing by the processor 6. In addition, the display device 7 displays various types of information relating to the endoscopic system 1. The display device 7 is configured using a display panel and the like of liquid crystal or organic EL (Electro Luminescence).

The light source device 8 emits illumination light from the distal end portion 101 side of the insertion portion 100 of the endoscope 2 toward the subject via the connector unit 5 and the transmission cable 3. The light source device 8 is configured using a white light emitting diode (LED) or the like that emits white light. Incidentally, a simultaneous illumination system is adopted for the light source device 8 in the first embodiment, but a frame-sequential illumination system may be used.

Main Part of Endoscopic System

Figure 2:
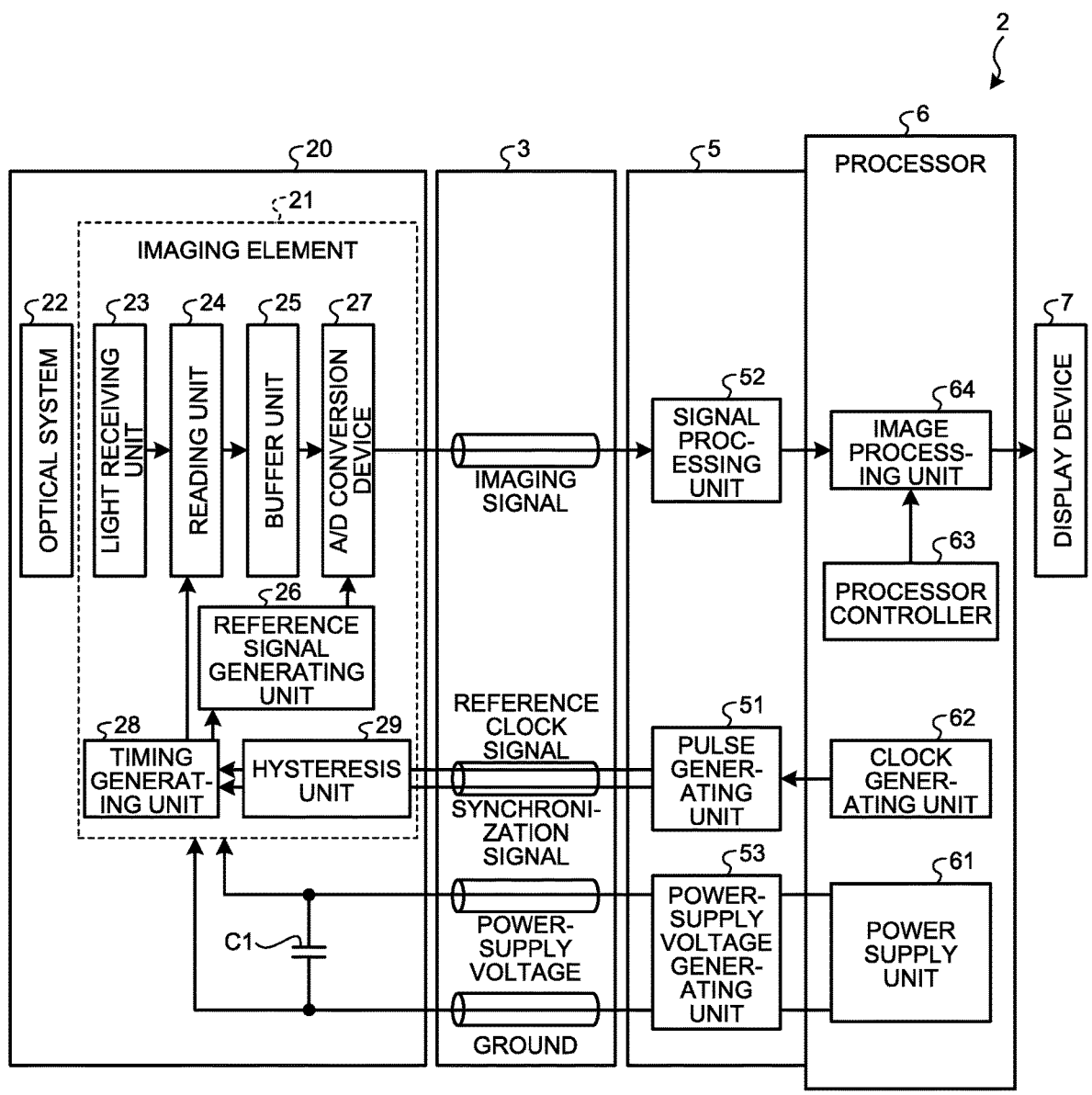
FIG. 2 is a block diagram illustrating a function of the main part of the endoscopic system according to the first embodiment of the disclosure.

Next, a function of the main part of the endoscopic system 1 will be described. FIG. 2 is a block diagram illustrating the function of the main part of the endoscopic system 1.

Configuration of Endoscope

First, a configuration of the endoscope 2 will be described.

The endoscope 2 illustrated in FIG. 2 includes the imaging device 20, the transmission cable 3, and the connector unit 5. The imaging device 20 includes an imaging element 21 (imaging chip), and an optical system 22 that forms a subject image on the imaging element 21.

The imaging element 21 includes: a light receiving unit 23 that has a plurality of pixels which are arranged in a matrix direction in a two-dimensional matrix, receive light from the outside, and generate and output an imaging signal in response to the amount of received light; a reading unit 24 that sequentially reads the imaging signal, photoelectrically converted by the light receiving unit 23, for each column; a buffer unit 25 (buffer circuit) that performs impedance conversion of a voltage of the imaging signal sequentially read by the reading unit 24, amplifies the signal by one time with a voltage follower, and outputs the amplified signal; a reference signal generating unit 26 (reference signal generating circuit) that generates and outputs a reference signal which has a fluctuation component of the same phase as the imaging signal generated by the light receiving unit 23 and is used for correction processing of the imaging signal; an A/D conversion device 27 (A/D conversion circuit) that samples the imaging signal output from the buffer unit 25 and the reference signal generated from the reference signal generating unit 26 at the same timing, converts the signal into a digital imaging signal and outputs the digital imaging sig to the outside; a timing generating unit 28 that generates a timing signal based on a reference clock signal and a synchronization signal; and a hysteresis unit 29 that performs waveform shaping of the reference clock signal and the synchronization signal input from the connector unit 5 via the transmission cable 3 and outputs the reference clock signal and the synchronization signal which have been subjected to the waveform shaping to the timing generating unit 28. In addition, the imaging element 21 receives a power-supply voltage VDD (for example, 3.3 V) generated in a power supply unit 61 of the processor 6, which will be described later, together with a ground GND via the transmission cable 3. A capacitor C1 for power supply stabilization is provided between the power-supply voltage VDD and the ground GND to be supplied to the imaging element 21. Incidentally, a detailed configuration of the imaging element 21 will be described later with reference to FIG. 3.

The optical system 22 is configured using a plurality of lenses and a prism, and forms a subject image on the light receiving unit 23 of the imaging element 21.

The connector unit 5 includes: a pulse generating unit 51 that generates a synchronization signal (including a horizontal synchronization signal and a vertical synchronization signal) representing a start position of each frame based on a reference clock signal (for example, a clock signal of 27 MHz), which is supplied from the processor 6 and serves as a reference of an operation of each component of the endoscope 2, and outputs the synchronization signal together with the reference clock signal to the timing generating unit 28 of the imaging device 20 via the transmission cable 3; a signal processing unit 52 that is configured using a field programmable gate array (FPGA), an application specific integrated circuit (ASIC), or the like, performs predetermined signal processing, for example, noise reduction processing, on a digital imaging signal output from the imaging device 20 via the transmission cable 3, and outputs the processed signal to the processor 6; and a power-supply voltage generating unit 53 that is configured using a regulator or the like, generates a power-supply voltage necessary to drive the imaging element 21 from power supply supplied from the processor 6, and outputs the generated power-supply voltage to the imaging element 21.

Configuration of Processor

Next, a configuration of the processor 6 will be described.

The processor 6 includes: a power supply unit 61 that generates a power-supply voltage and supplies this generated power-supply voltage VDD to the power-supply voltage generating unit 53 of the connector unit 5 together with the ground GND; a clock generating unit 62 that generates a reference clock signal serving as a reference of an operation of each component of the endoscopic system 1 and outputs the reference clock signal to the pulse generating unit 51 of the connector unit 5; a processor controller 63 that is configured using a central processing unit (CPU) or the like and comprehensively controls the entire endoscopic system 1; and an image processing unit 64 that performs image processing, such as synchronization processing, white balance (WB) adjustment processing, gain adjustment processing, gamma correction processing, digital analog (D/A) conversion processing, and format conversion processing, on the digital imaging signal input from the endoscope 2 to convert the digital imaging signal to an image signal, and outputs the image signal to the display device 7.

Configuration of Imaging Element

Figure 3:
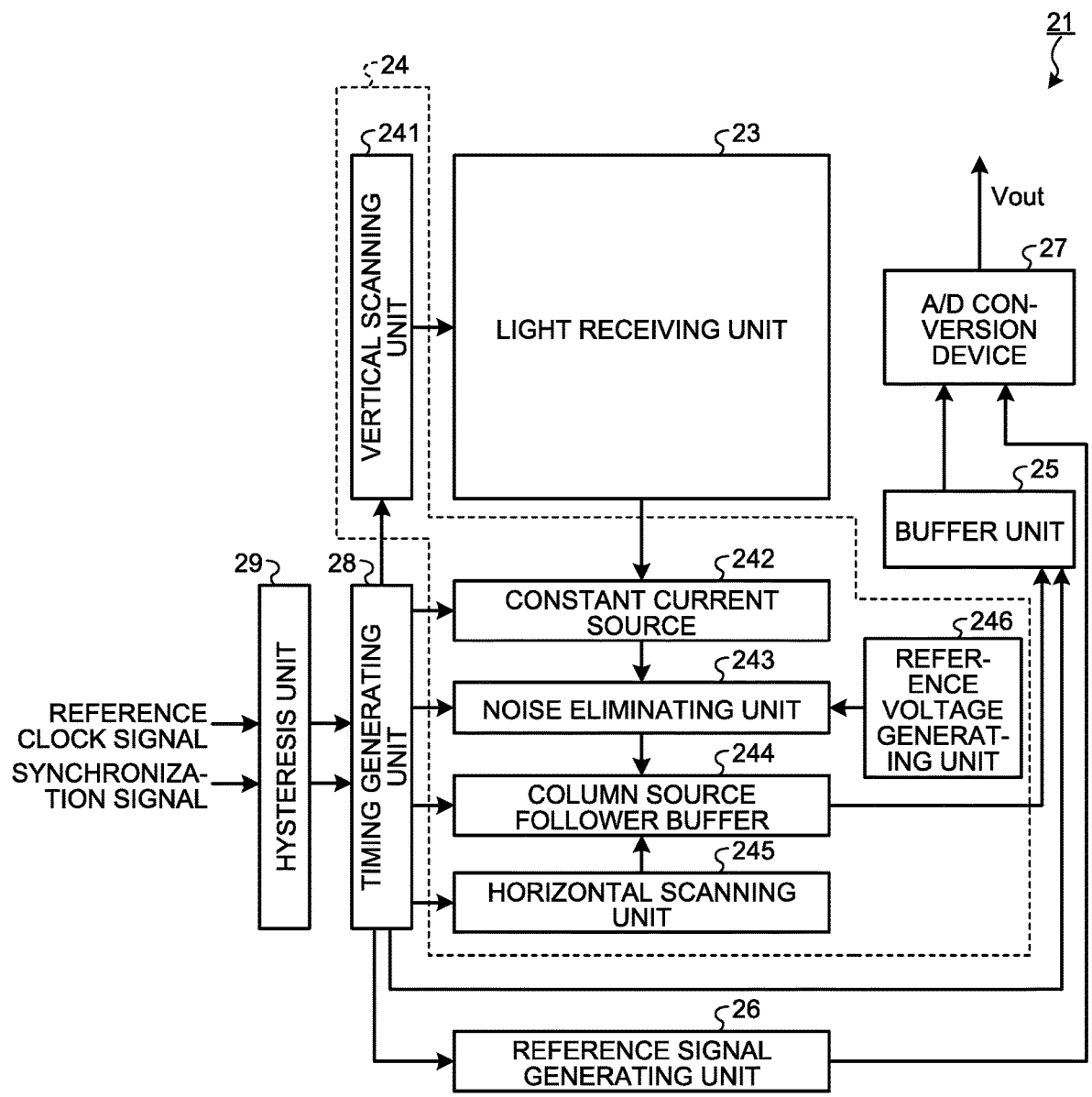
FIG. 3 is a block diagram illustrating a detailed configuration of an imaging element illustrated in FIG. 2.

Next, a detailed configuration of the above-described imaging element 21 will be described. FIG. 3 is a block diagram illustrating the detailed configuration of the imaging element 21 illustrated in FIG. 2.

As illustrated in FIG. 3, the imaging element 21 includes: the light receiving unit 23, the reading unit 24, the buffer unit 25, the reference signal generating unit 26, the A/D conversion device 27, the timing generating unit 28, and the hysteresis unit 29.

The light receiving unit 23 has a plurality of pixels which are arranged in a matrix direction in a two-dimensional matrix, receive light from the outside, and generate and output an imaging signal in response to the amount of received light. Incidentally, a configuration of the pixel in the light receiving unit 23 will be described in detail in FIG. 4 to be described later.

The reading unit 24 sequentially reads an imaging signal from each of the plurality of pixels of the light receiving unit 23 to be described later, and outputs the imaging signal to the buffer unit 25. The reading unit 24 includes a vertical scanning unit 241 (row selection circuit), a constant current source 242, a noise eliminating unit 243 (noise eliminating circuit), a column source follower buffer 244, a horizontal scanning unit 245 (horizontal scanning circuit), and a reference voltage generating unit 246.

The vertical scanning unit 241 applies drive signals $\phi T<M>$ and $\phi R<M>$ to a selected row (horizontal line) $<M>$ ($M=0, 1, 2, \ldots, m-1$, and m) of the light receiving unit 23 based on a drive signal ($\phi T$, $\phi R$, or the like) input from the timing generating unit 28 to cause each of pixels 230 of the light receiving unit 23 to be driven by the constant current source 242, transfers an imaging signal and a noise signal at the time of pixel resetting to a vertical transfer line 239 (first transfer line) to be described later, and outputs the signals to the noise eliminating unit 243.

The noise eliminating unit 243 eliminates an output variation of each of the pixels 230 to be described later and the noise signal at the time of pixel resetting, and outputs the imaging signal, which has been photoelectrically converted by each of the pixels 230 to be described later, to the column source follower buffer 244.

The column source follower buffer 244 holds the imaging signal from which noise has been eliminated by the noise eliminating unit 243 based on the drive signal input from the horizontal scanning unit 245, amplifies the held imaging signal, and outputs the amplified signal to the buffer unit 25.

The horizontal scanning unit 245 applies a drive signal $\phi HCLK<N>$ to a selected column (vertical line) $<N>$ ($N=0, 1, 2, \ldots, n-1$, and n) of the light receiving unit 23 based on a drive signal ($\phi HCLK$) input from the timing generating unit 28, transfers the imaging signal, which has been photoelectrically converted by each of the pixels 230, to a horizontal transfer line 257 to be described later via the noise eliminating unit 243 and the column source follower buffer 244, and outputs the signal to the buffer unit 25.

The reference voltage generating unit 246 generates a clamp voltage VCLP of the noise eliminating unit 243 from the same power-supply voltage VDD as that of the light receiving unit 23. Incidentally, details of a circuit of the reference voltage generating unit 246 will be described later with reference to FIG. 5.

The buffer unit 25 performs impedance conversion on a voltage of an imaging signal sequentially output from the column source follower buffer 244, amplifies the signal by one time with a voltage follower, and outputs the amplified signal to the A/D conversion device 27. Incidentally, details of the circuit of the buffer unit 25 will be described later with reference to FIG. 4.

The reference signal generating unit 26 generates a reference signal, which has a fluctuation component of the same phase as the imaging signal generated by the light receiving unit 23 and is used for correction processing of the imaging signal, and outputs the generated reference signal to the A/D conversion device 27. Incidentally, details of a circuit of the reference signal generating unit 26 will be described later with reference to FIG. 6.

The A/D conversion device 27 samples the imaging signal output from the buffer unit 25 and the reference signal generated from the reference signal generating unit 26 at the same timing, converts the signal to a digital imaging signal (Vout) and outputs the digital imaging signal (Vout) to the outside.

The timing generating unit 28 generates various drive signals based on the reference clock signal and the synchronization signal input from the hysteresis unit 29, and outputs the generated signals to the reading unit 24, the buffer unit 25, the reference signal generating unit 26, and the A/D conversion device 27 which will be described later.

The hysteresis unit 29 performs waveform shaping on the reference clock signal and the synchronization signal input via the transmission cable 3, and outputs the reference clock signal and the synchronization signal that have been subjected to the waveform shaping to the timing generating unit 28.

Configuration of Circuit of Imaging Element

Figure 4:
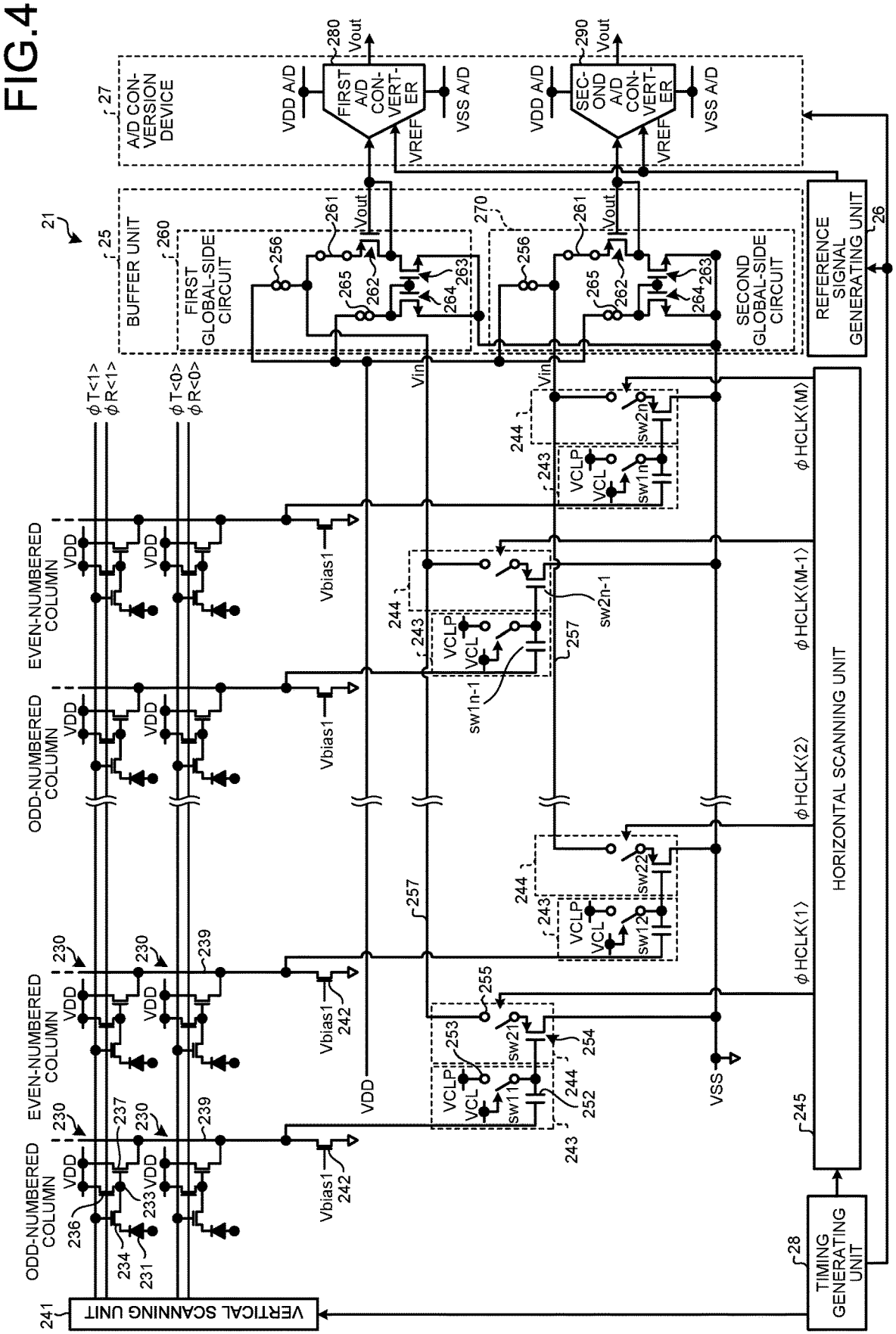
FIG. 4 is a circuit diagram schematically illustrating a configuration of the imaging element according to the first embodiment.

Next, the circuit of the above-described imaging element 21 will be described in detail. FIG. 4 is a circuit diagram schematically illustrating the configuration of the imaging element 21.

Configuration of Pixel

First, the configuration of the pixel 230 will be described. As illustrated in FIG. 4, the multiple pixels 230 are arranged in the two-dimensional matrix in the above-described light receiving unit 23. Each of the pixels 230 includes a photoelectric conversion element 231 (photodiode), a charge converter 233, a transfer transistor 234 (first transfer unit), a pixel resetting unit 236 (transistor), and a pixel source follower transistor 237.

The photoelectric conversion element 231 photoelectrically converts incident light into a signal charge amount corresponding to the amount of light, and accumulates the signal charge amount. The photoelectric conversion element 231 has a cathode side connected to one end side of the transfer transistor 234 and an anode side connected to the ground GND.

The charge converter 233 is formed of a floating diffusion capacitor (FD), and converts the charge accumulated in the photoelectric conversion element 231 into a voltage.

The transfer transistor 234 transfers the charge from the photoelectric conversion element 231 to the charge converter 233. A gate of the transfer transistor 234 is connected with a signal line to which a drive signal (row selection pulse) φR and a drive signal φT are supplied, and the other end side thereof is connected with the charge converter 233. The transfer transistor 234 is turned into an ON state when the drive signal φR and the drive signal φT are supplied from the vertical scanning unit 241 via the signal line, and transfers the charge from the photoelectric conversion element 231 to the charge converter 233.

The pixel resetting unit 236 resets the charge converter 233 to a predetermined potential. The pixel resetting unit 236 has one end side connected to the power-supply voltage VDD and the other end side connected to the charge converter 233, and a gate thereof is connected with a signal line to which the drive signal φR is supplied. The pixel resetting unit 236 is turned into an ON state when the drive signal φR is supplied from the vertical scanning unit 241 via the signal line, and releases the signal charge accumulated in the charge converter 233 and resets the charge converter 233 to a predetermined potential.

The pixel source follower transistor 237 has one end side connected to the power-supply voltage VDD (for example, 3.3 V) and the other end side connected to the vertical transfer line 239, and a signal (an imaging signal or a signal at the time of resetting), which has been subjected to voltage conversion in the charge converter 233, is input to a gate thereof. When the drive signal φT is supplied to the gate of the transfer transistor 234, the pixel source follower transistor 237 reads the charge from the photoelectric conversion element 231 after a selection operation to be described later, and transfers the imaging signal after being subjected to the voltage conversion in the charge converter 233 to the vertical transfer line 239.

The constant current source 242 has one end side connected to the vertical transfer line 239 and the other end side connected to the ground GND, and a bias voltage Vbias1 is applied to a gate thereof. The constant current source 242 drives the pixel 230 and outputs the output of the pixel 230 to the vertical transfer line 239. The signal output to the vertical transfer line 239 is input to the noise eliminating unit 243.

Configuration of Noise Eliminating Unit

Next, a configuration of the noise eliminating unit 243 will be described.

The noise eliminating unit 243 illustrated in FIG. 4 is provided for each column of the pixels 230. Specifically, the noise eliminating unit 243 is provided for each of the vertical transfer lines 239. The noise eliminating unit 243 includes a transfer capacitor 252 (AC coupling capacitor) and a clamp switch 253 (transistor). Incidentally, the noise eliminating unit 243 functions as a clamp circuit in the first embodiment.

The transfer capacitor 252 has one end side connected to the vertical transfer line 239 and the other end side connected to a column source follower transistor 254 of a column source follower buffer 244 to be described later.

The clamp switch 253 has one end side connected with a signal line to which the clamp voltage VCLP is supplied from the reference voltage generating unit 246 and the other end side connected between the transfer capacitor 252 and the column source follower buffer 244, and a drive signal φVCL is supplied to a gate thereof from the timing generating unit 28. The imaging signal input to the noise eliminating unit 243 is an optical noise sum signal including a noise component.

When the drive signal φVCL is input from the timing generating unit 28 to the gate of the clamp switch 253 in the noise eliminating unit 243 configured in this manner, the clamp switch 253 is turned into the ON state, and the transfer capacitor 252 is reset by the clamp voltage VCLP supplied from the reference voltage generating unit 246. The imaging signal from which noise is eliminated by the noise eliminating unit 243 is input to the gate of the column source follower buffer 244. The noise eliminating unit 243 does not require a capacitor for sampling (sampling capacitor), and thus, it is enough when a capacitance of the transfer capacitor 252 (AC coupling capacitor) is a capacitance sufficient for an input capacitance of the column source follower buffer 244. Further, it is possible to reduce an occupied area occupied in the imaging element 21 as the sampling capacitor is not provided in the noise eliminating unit 243.

Configuration of Column Source Follower Buffer

Next, the configuration of the column source follower buffer 244 will be described.

The column source follower buffer 244 illustrated in FIG. 4 is provided for each column of the pixels 230. Specifically, the column source follower buffer 244 is provided for each of the vertical transfer lines 239. The column source follower buffer 244 includes the column source follower transistor 254 and a column selection switch 255. Incidentally, the column source follower buffer 244 functions as a column-side circuit in the first embodiment.

The column source follower transistor 254 has one end side connected to a power-supply voltage VSS (hereinafter referred to as the "ground GND"), the other end side connected to one end side of the column selection switch 255, and a gate to which the imaging signal from which noise has been eliminated by the noise eliminating unit 243 is input.

The column selection switch 255 has one end side connected to the other end side of the column source follower transistor 254, and the other end side connected to the horizontal transfer line 257. The column selection switch 255 is configured using a transistor and has a gate to which a signal line for supplying a drive signal ϕHCLK<M> from the horizontal scanning unit 245 is connected. The column selection switch 255 is turned into an ON state when the drive signal ϕHCLK<M> is supplied from the horizontal scanning unit 245, and transfers the imaging signal from which noise has been eliminated by the noise eliminating unit 243 to the horizontal transfer line 257. Incidentally, a horizontal resetting transistor (not illustrated) is connected to the horizontal transfer line 257, the horizontal resetting transistor is set to the ON state as a drive signal is input to the horizontal resetting transistor from the timing generating unit 28, thereby resetting the horizontal transfer line 257.

In the column source follower buffer 244 configured in this manner, the column selection switch 255 is set to the ON state when the drive signal ϕHCLK<M> is applied to the column selection switch 255 from the timing generating unit 28, and the imaging signal from which noise has been eliminated by the noise eliminating unit 243 is sequentially input to the buffer unit 25 via the horizontal transfer line 257.

Configuration of Buffer Unit

Next, the configuration of the buffer unit 25 will be described.

The buffer unit 25 illustrated in FIG. 4 is connected with the column source follower buffer 244 sequentially selected by the horizontal scanning unit 245 to form the voltage follower circuit, perform impedance conversion on a voltage of the input imaging signal, and output the signal to the A/D conversion device 27. Specifically, the buffer unit 25 is connected with the column source follower buffer 244 sequentially selected by the horizontal scanning unit 245 to amplify the input imaging signal by one time with the voltage follower, and output the amplified signal to the A/D conversion device 27. The buffer unit 25 includes a first global-side circuit 260 and a second global-side circuit 270 provided, respectively, in the odd-numbered column and the even-numbered column of the pixels 230. Incidentally, the first global-side circuit 260 and the second global-side circuit 270 function as impedance converters.

The first global-side circuit 260 includes a constant current source 256, a switch 261, a first transistor 262, a second transistor 263, a third transistor 264, and a constant current source 265.

The constant current source 256 has one end side connected to the horizontal transfer line 257, and the other end side connected to the power-supply voltage VDD. The constant current source 256 reads an imaging signal to the horizontal transfer line 257. The imaging signal read to the horizontal transfer line 257 is input to a source side of the first transistor 262 via the switch 261 to be described later. Incidentally, the constant current source 256 functions as a first constant current source in the first embodiment.

The switch 261 has one end side connected to the column selection switch 255 of the column source follower buffer 244 via the horizontal transfer line 257, and the other end side connected to the source side of the first transistor 262. The switch 261 has a resistance value similar to that of the column selection switch 255 of the column source follower buffer 244, and is configured using, for example, a transistor. The switch 261 is provided constantly in the ON state, and connects the horizontal transfer line 257 and the first transistor 262.

The first transistor 262 has one end side (source side) connected to the column selection switch 255 of the column source follower buffer 244 via the switch 261 and the horizontal transfer line 257, the other end side (drain side) connected to one end side (drain side) of the second transistor 263, and a gate connected to the A/D conversion device 27. The first transistor 262 is configured using a PMOS.

The second transistor 263 has one end side (drain side) connected to the other end side (drain side) of the first transistor 262 and the gate of the first transistor 262, the other end side (source side) connected to the ground GND, and a gate connected to the constant current source 265. The second transistor 263 is configured using an NMOS.

The third transistor 264 has one end side (drain side) connected to the constant current source 265 (second constant current source), the other end side (source side) connected to the ground GND, and a gate connected to the constant current source 265.

The first global-side circuit 260 configured in this manner is connected with the column source follower buffer 244 (column-side circuit) of the odd-numbered column sequentially selected by the horizontal scanning unit 245 to form a voltage follower circuit, perform impedance conversion on a voltage of an imaging signal (Vin) input from the column source follower buffer 244, amplify the signal by one time with the voltage follower, and output the imaging signal (Vout) to the A/D conversion device 27.

The second global-side circuit 270 has the same configuration as the above-described first global-side circuit 260, and includes the constant current source 256, the switch 261, the first transistor 262, the second transistor 263, the third transistor 264, and the constant current source 265.

The second global-side circuit 270 configured in this manner is connected with the column source follower buffer 244 (column-side circuit) of the even-numbered column sequentially selected by the horizontal scanning unit 245 to form a voltage follower circuit, perform impedance conversion on the voltage of the input imaging signal (Vin), amplify the signal by one time with the voltage follower, and output the imaging signal (Vout) to the A/D conversion device 27.

The reference signal generating unit 26 generates a reference signal, which has a fluctuation component of the same phase as the imaging signal generated by the pixel 230 and is used for correction processing of the imaging signal, and outputs the generated reference signal to the A/D conversion device 27. Incidentally, details of a circuit of the reference signal generating unit 26 will be described later with reference to FIG. 6.

The A/D conversion device 27 includes a first A/D converter 280, which converts an analog imaging signal output from the pixels 230 of the odd-numbered column into a digital imaging signal and outputs the digital imaging signal to the outside, and a second A/D converter 290, which converts an analog imaging signal output from the pixel 230 of the even-numbered column into a digital imaging signal and outputs the digital imaging signal to the outside, the first A/D converter 280 and the second A/D converter 290 provided, respectively, for the odd-numbered column and the even-numbered column in the light receiving unit 23. Incidentally, details of circuits of the first A/D converter 280 and the second A/D converter 290 will be described later with reference to FIG. 7.

Configuration of Reference Voltage Generating Unit

Figure 5:
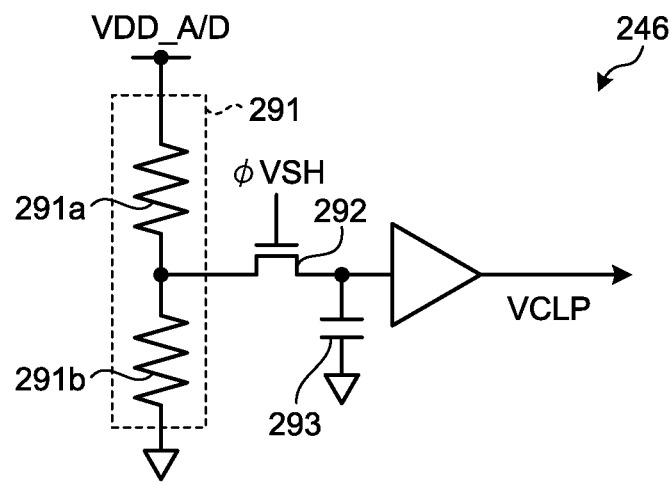
FIG. 5 is a circuit diagram illustrating a configuration of a reference voltage generating unit according to the first embodiment.

Next, a configuration of the reference voltage generating unit 246, which has been described above in FIG. 3, will be described. FIG. 5 is a circuit diagram illustrating the configuration of the reference voltage generating unit 246.

The reference voltage generating unit 246 (constant voltage signal generating unit) illustrated in FIG. 5 includes: a resistance voltage dividing circuit 291, which is formed of two resistors 291a and 291b and has one end connected to VDD_A/D (for example, 3.3 V) and the other end connected to the ground GND; a switch 292 (transistor) driven using the drive signal ϕVSH applied from the timing generating unit 28; and a sampling capacitor 293 (capacitor) configured for release from fluctuation independently of power supply.

The reference voltage generating unit 246 configured in this manner generates the clamp voltage VCLP of the noise eliminating unit 243 at a timing driven by the drive signal ϕVSH due to driving of the switch 292, and outputs the clamp voltage VCLP to the noise eliminating unit 243.

Configuration of Reference Signal Generating Unit

Figure 6:
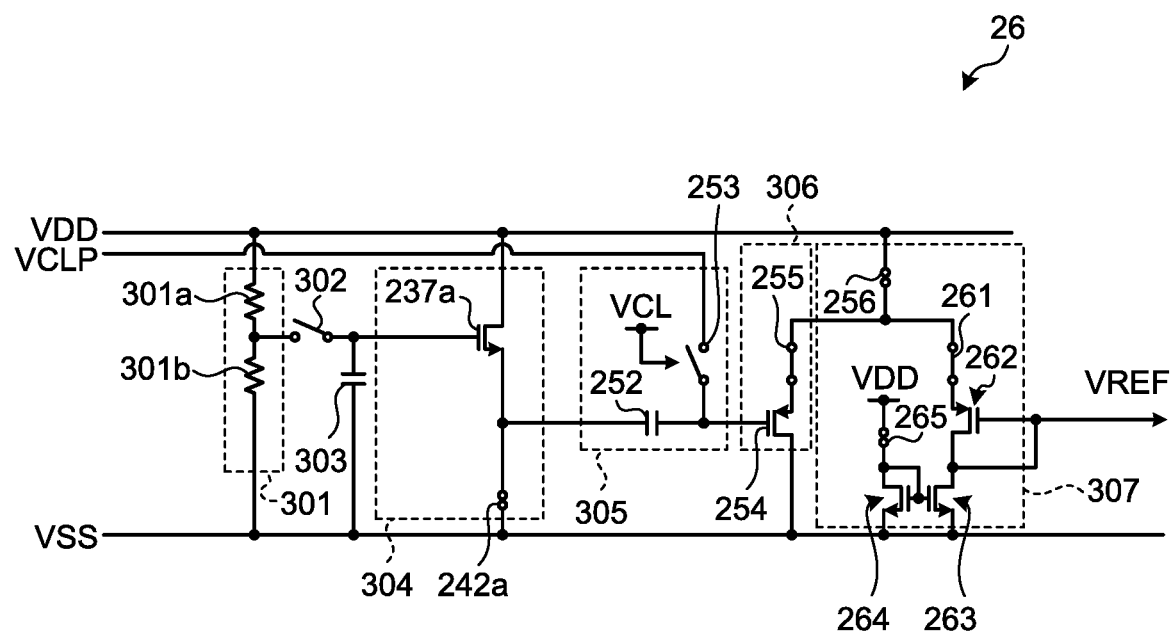
FIG. 6 is a circuit diagram schematically illustrating a configuration of a reference signal generating unit according to the first embodiment.

Next, a detailed configuration of the reference signal generating unit 26 described above in FIGS. 3 and 4 will be described. FIG. 6 is a circuit diagram schematically illustrating the configuration of the reference signal generating unit 26.

The reference signal generating unit 26 illustrated in FIG. 6 includes: a resistance dividing circuit 301 formed of two resistors 301a and 301b; a switch 302 (transistor) driven by a drive signal applied from the timing generating unit 28; a sampling capacitor 303 (capacitor) configured for release from fluctuation independently of the power supply; a pixel equivalent circuit 304; a noise elimination equivalent circuit 305; a column equivalent circuit 306; and a buffer equivalent circuit 307.

The pixel equivalent circuit 304 forms a circuit equivalent to each of the pixel source follower transistor 237 of the pixel 230 and the constant current source 242, and includes a pixel source follower transistor 237a and a constant current source 242a that drives the pixel source follower transistor 237a.

The pixel source follower transistor 237a has one end side (drain side) connected to the power-supply voltage VDD, the other end side (source side) connected to the constant current source 242a, and a gate connected with a signal line to which a signal transferred from the sampling capacitor 303 is transferred.

The constant current source 242a has one end side connected to the pixel source follower transistor 237a, and the other end side connected to the ground GND. The constant current source 242a drives the pixel source follower transistor 237a, and outputs the output of the pixel source follower transistor 237a to the noise elimination equivalent circuit 305.

The noise elimination equivalent circuit 305 forms a circuit equivalent to the above-described noise eliminating unit 243, and includes the transfer capacitor 252 (AC coupling capacitor) and the clamp switch 253. Since the noise elimination equivalent circuit 305 is the circuit equivalent to the above-described noise eliminating unit 243, the detailed description thereof will be omitted.

The column equivalent circuit 306 forms a circuit equivalent to the above-described column source follower buffer 244, and includes the column source follower transistor 254 and the column selection switch 255. Since the column equivalent circuit 306 is the circuit equivalent to the above-described column source follower buffer 244, the detailed description thereof will be omitted.

The buffer equivalent circuit 307 forms a circuit equivalent to the above-described first global-side circuit 260, and includes the constant current source 256, the switch 261, the first transistor 262, the second transistor 263, the third transistor 264, and the constant current source 265. Since the buffer equivalent circuit 307 is the circuit equivalent to the above-described first global-side circuit 260, the detailed description thereof will be omitted.

The reference signal generating unit 26 configured in this manner generates a reference signal (VREF), which has a fluctuation component of the same phase as the imaging signal generated by the pixel 230 and is used for correction processing of the imaging signal, and outputs the generated reference signal (VREF) to the A/D conversion device 27.

Configuration of First A/D Converter

Figure 7:
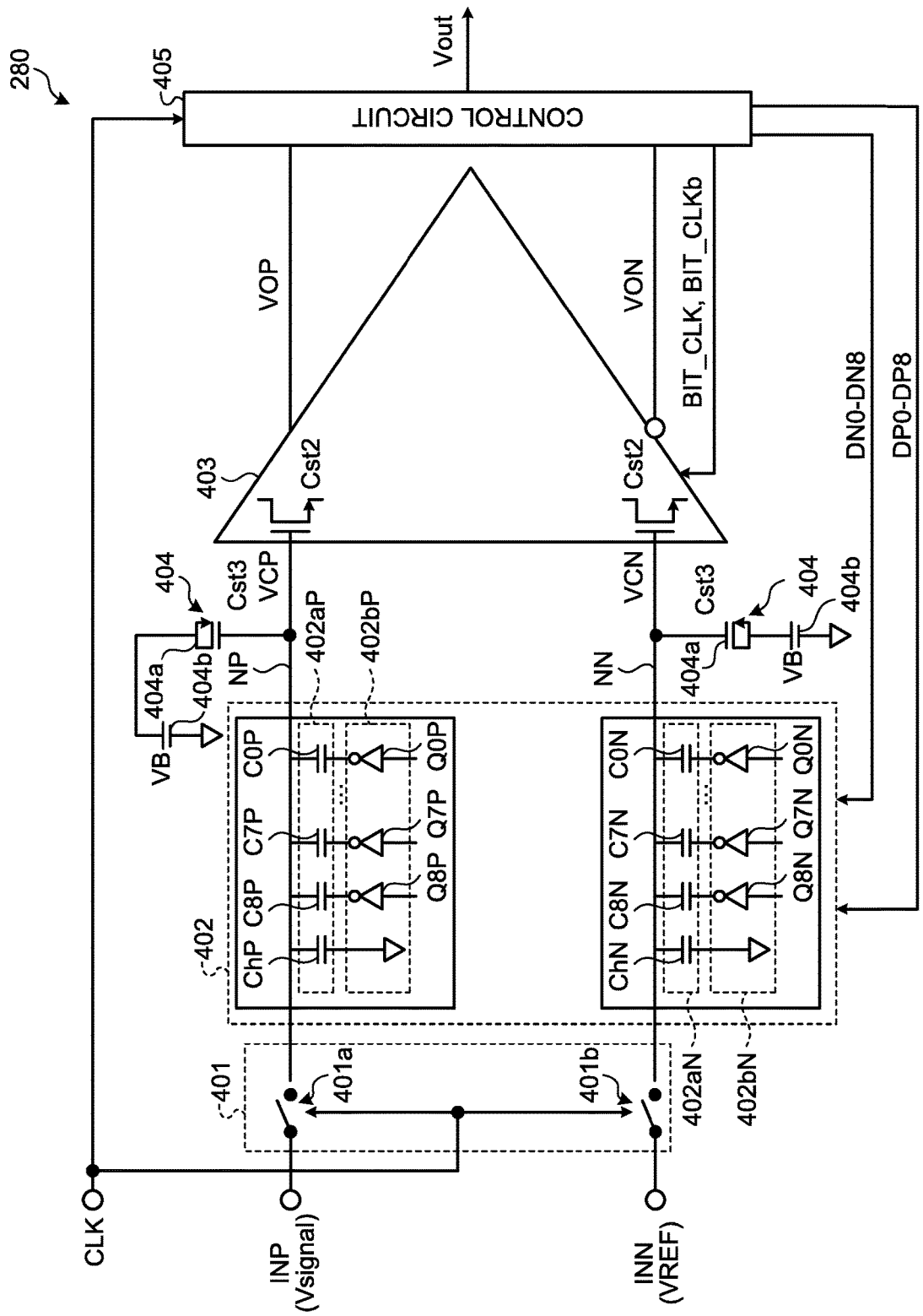
FIG. 7 is a circuit diagram schematically illustrating a configuration of a first A/D converter according to the first embodiment.

Next, a configuration of the first A/D converter 280 will be described. FIG. 7 is a circuit diagram for schematically describing the configuration of the first A/D converter 280. Incidentally, the first A/D converter 280 and the second A/D converter 290 have the same circuit configuration, and thus, only the configuration of the first A/D converter 280 will be described hereinafter, and the configuration of the second A/D converter 290 will not be described. In addition, the first A/D converter 280 illustrated in FIG. 7 is a successive approximation type A/D conversion device and is an A/D conversion device with a 9-bit output, but the disclosure is not limited thereto, and the number of output bits can be changed as appropriate. Incidentally, the first A/D converter 280 is not necessarily the successive approximation type A/D conversion device, but is preferably an A/D conversion device capable of saving power, and may be, for example, a Nyquist A/D conversion device.

The first A/D converter 280 illustrated in FIG. 7 includes a sampling circuit 401, a capacitive DAC circuit 402, a comparison circuit 403, a correction circuit 404, and a control circuit 405.

The sampling circuit 401 performs track and hold on a pair of an imaging signal (Vsignal) and the reference signal (VREF) constituting a differential input signal at the same timing based on the clock signal CLK input from the timing generating unit 28, thereby sampling the analog imaging signal and reference signal. The sampling circuit 401 includes a switch 401a and a switch 401b.

The switch 401a establishes conduction between the above-described first global-side circuit 260 and the capacitive DAC circuit 402 in an ON state, and establishes a high impedance state between the first global-side circuit 260 and the capacitive DAC circuit 402 in an OFF state. The switch 401a receives the analog imaging signal via a non-inverting input terminal INP. The switch 401a holds and samples the analog imaging signal in a capacitance unit 402aP, which will be described later, at the timing when switching from the ON state to the OFF state. The switch 401a switches between the ON state and the OFF state based on the clock signal CLK input from the timing generating unit 28.

The switch 401b establishes conduction between the above-described reference signal generating unit 26 and the capacitive DAC circuit 402 in an ON state, and establishes a high impedance state between the reference signal generating unit 26 and the capacitive DAC circuit 402 in an OFF state. The switch 401b receives the analog reference signal via an inverting input terminal INN. The switch 401b holds and samples the analog reference signal in a capacitance unit 402aN, which will be described later, at the timing when switching from the ON state to the OFF state. The switch 401b is switched between the ON state and the OFF state based on the clock signal CLK input from the timing generating unit 28.

The capacitive DAC circuit 402 generates an analog signal based on digital signals (DN0 to DN8 and DP0 to DP8) generated by the control circuit 405, and subtracts a referring signal (another reference signal different from the reference signal VREF) from each of the imaging signal and the reference signal held and sampled by the sampling circuit 401 to acquire cumulative residuals between the differential input signal and the 9-bit digital signals D0 to D8. The capacitive DAC circuit 402 outputs the subtraction results obtained by subtracting the referring signal from each of the imaging signal and the reference signal to the comparison circuit 403 as analog imaging signal (INP) and reference signal (INN) on which the cumulative residuals have been reflected. The capacitive DAC circuit 402 includes the capacitance unit 402aN, a drive unit 402bN, the capacitance unit 402aP, and a drive unit 402bP.

The capacitance unit 402aP has an attenuation capacitor ChP and binary capacitors C0P to C8P. The attenuation capacitor ChP is connected between a signal node NP corresponding to a wiring connected to the switch 401a and the ground GND. In addition, each of the binary capacitors C0P to C8P is connected between the signal node NP and each of output portions of the drive unit 402bP. That is, each of the binary capacitors C0P to C8P has one electrode commonly connected to the signal node NP and the other electrode individually connected to output portions of inverters Q0P to Q8P that constitute the drive unit 402bP to be described later. The binary capacitors C0P to C8P are arranged corresponding to the digital signals DP0 to DP8 generated by the control circuit 405. Capacitance values of the respective binary capacitors C0P to C8P are different. For example, a capacitance value of the capacitor C(n+1)P corresponding to a digital signal DP(n+1) is twice a capacitance value of a capacitor CnP corresponding to a digital signal DPn (n is an Integer from 0 to 7). That is, the capacitance value of each of the binary capacitors C0P to C8P is weighted by a binary number according to the order of each bit of the digital signals DP0 to DP8.

The capacitance unit 402aN has an attenuation capacitor ChN and binary capacitors C0N to C8N similarly to the capacitance unit 402aP. The attenuation capacitor ChN is connected between a signal node NN corresponding to a wiring connected to the switch 401b and the ground GND. In addition, each of the binary capacitors C0N to C8N is connected between the signal node NN and each of output portions of the drive unit 402bN. That is, each of the binary capacitors C0N to C8N has one electrode commonly connected to the signal node NN, and the other electrode individually connected to output portions of inverters Q0N to Q8N constituting the drive unit 402bN to be described later. The binary capacitors C0N to C8N are arranged corresponding to the digital signals DN0 to DN8 generated by the control circuit 405. Incidentally, capacitance values of the binary capacitors C0N to C8N are also weighted by a binary number in the same manner as the binary capacitors C0P to C8P. In addition, each of the capacitance values of the binary capacitors C0N to C8N constituting the capacitance unit 402aN is set to be the same as each of the capacitance values of the binary capacitors C0P to C8P constituting the capacitance unit 402aP.

The drive unit 402bP includes the inverters Q0P to Q8P. The power-supply voltage VDD_A/D is supplied to the inverters Q0P to Q8P. This means that an amplitude of an analog signal output from each of the inverters Q0P to Q8P is equal to the power-supply voltage VDD_A/D. The inverters Q0P to Q8P are arranged corresponding to the digital signals DP0 to DP8 generated by the control circuit 405. Each bit of the digital signals DP0 to DP8 is input from the control circuit 405 to each of the inverters Q0P to Q8P. In addition, the output portions of the inverters Q0P to Q8P are connected to the other electrodes of the binary capacitors C0P to C8P, respectively.

The inverters Q0P to Q8P generate referring signals by inverting the digital signals DP0 to DP8 input from the control circuit 405. The plurality of binary capacitors C0P to C8P included in the capacitance unit 402aP extract a charge based on the referring signal from a charge based on the analog imaging signal Vsignal held in the attenuation capacitor ChP by charge redistribution to subtract the referring signal from the imaging signal Vsignal. The capacitance unit 402aP outputs an analog signal VCP, which is the subtraction result, to the comparison circuit 403.

The drive unit 402bN includes the inverters Q0N to Q8N. The power-supply voltage VDD_A/D is supplied to the inverters Q0N to Q8N. This means that an amplitude of a reference signal output from each of the inverters Q0N to Q8N is equal to the power-supply voltage VDD_A/D. The inverters Q0N to Q8N are arranged corresponding to the digital signals DN0 to DN8 generated by the control circuit 405. Each bit of the digital signals DN0 to DN8 is input from the control circuit 405 to each of the inverters Q0N to Q8N. In addition, the output portions of the inverters Q0N to Q8N are connected to the other electrodes of the binary capacitors C0N to C8N, respectively.

The inverters Q0N to Q8N generate the referring signals by inverting the digital signals DN0 to DN8 input from the control circuit 405. The plurality of binary capacitors C0N to C8N included in the capacitance unit 402aN extract a charge based on the referring signal from a charge based on the analog reference signal VREF held in the attenuation capacitor ChN by charge redistribution to subtract the referring signal from the analog reference signal VREF. The capacitance unit 402aN outputs an analog signal VCN which is the subtraction result.

The comparison circuit 403 (comparator) compares the analog imaging signal input from the capacitive DAC circuit 402 with the analog reference signal, and outputs a digital signal VOP and a digital signal VON indicating the comparison results in accordance with the magnitude relationship therebetween. Specifically, when a signal level of the analog imaging signal is higher than a signal level of the analog reference signal, the comparison circuit 403 outputs a high-level signal as the digital signal VOP, and outputs a low-level signal as the digital signal VON. Conversely, when the signal level of the analog imaging signal is lower than the signal level of the analog reference signal, the comparison circuit 403 outputs the low-level signal as the digital signal VOP and outputs the high-level signal as the digital signal VON. The comparison circuit 403 is controlled based on an internal clock signal BIT_CLK and an inverted internal clock signal BIT_CLKb generated by the control circuit 405 to be described later.

The correction circuit 404 is provided on the front side of the comparison circuit 403, and outputs a pair of voltage signals offsetting a parasitic capacitance in an input transistor of the comparison circuit 403 to the comparison circuit 403. Specifically, the correction circuit 404 offsets the parasitic capacitance (gate capacitance) of the input transistor of the comparison circuit 403 to correct a pair of analog signal voltages input to the comparison circuit 403, and outputs the correction results to the comparison circuit 403. The correction circuit 404 includes a correction transistor 404a that offsets the parasitic capacitance of the input transistor of the comparison circuit 403 and a bias circuit 404b that applies a bias voltage VB to the correction transistor 404a. A gate terminal of the correction transistor 404a is connected to an input terminal of the comparison circuit 403, and a drain terminal and a source terminal of the correction transistor 404a are connected to each other and connected to the bias circuit 404b. The correction transistor 404a forms a MOS capacitor between the gate terminal and the drain/source terminal commonly connected. The voltage dependency of the capacitance of the correction transistor 404a has a reverse characteristic to the voltage dependency of the input transistor of the comparison circuit 403. Incidentally, the voltage dependency of the correction transistor 404a will be described later.

The control circuit 405 functions as a successive approximation register (SAR) logic circuit, and sequentially determines a value of each bit of the digital signals DP0 to DP8 and the digital signals DN0 to DN8 corresponding to the digital signal VOP and the digital signal VON indicating the comparison results of the comparison circuit 403 according to a binary search algorithm. The control circuit 405 supplies the digital signals DP0 to DP8 and the digital signals DN0 to DN8 corresponding to the digital signal VOP and the digital signal VON to the capacitive DAC circuit 402. Among these, the control circuit 405 outputs the digital signals DP0 to DP8 as digital signals D0 to D8 representing A/D conversion results (Vout). In addition, the control circuit 405 generates the internal clock signal BIT_CLK and the inverted internal clock signal BIT_CLKb for control of the comparison circuit 403, and supplies the generated clock signals to the comparison circuit 403. The control circuit 405 is controlled based on the clock signal CLK generated by the timing generating unit 28. The control circuit 405 generates the internal clock signal BIT_CLK and the inverted internal clock signal BIT_CLKb while the clock signal CLK is at a high level.

The first A/D converter 280 configured in this manner sequentially acquires the A/D conversion results one bit by one bit in order from the most significant bit (D8) to the least significant bit (D0) of the digital signals D0 to D8. In the course of such A/D conversion, the comparison circuit 403 compares a signal level (voltage) of the analog imaging signal (INP) reflecting a cumulative residual error so far with a signal level (voltage) of the analog reference signal (INN) each time the above-described subtraction is performed by the capacitive DAC circuit 402.

In addition, a differential input range of the first A/D converter 280 is given as the following Formula (1).

$$V_{fs,pp} = 2 \frac{Cdac}{Cdac + Ch + Cst1 + Cst2 + Cst3} VDD\_A/D \quad (1)$$

Here, Cst1 represents a parasitic capacitance generated between metal wires (node wires), Cst2 represents an input capacitance of the comparison circuit 403, Cst3 represents a MOS capacitance generated by the correction transistor 404a, and Ch represents an attenuation capacitance of the capacitive DAC circuit 402.

When Ch is set such that Cdac=Ch+Cst1+Cst2+Cst3 in the above-described Formula (1), a gain coefficient becomes 1, and it is possible to secure a full-scale range. Thus, the capacitance of the correction transistor 404a is set such that the value of the MOS capacitance has the dependency of a bias voltage of a reverse characteristic to a gate capacitance of the input transistor of the comparison circuit 403 in the first embodiment.

Characteristics of Correction Transistor

Figure 8:
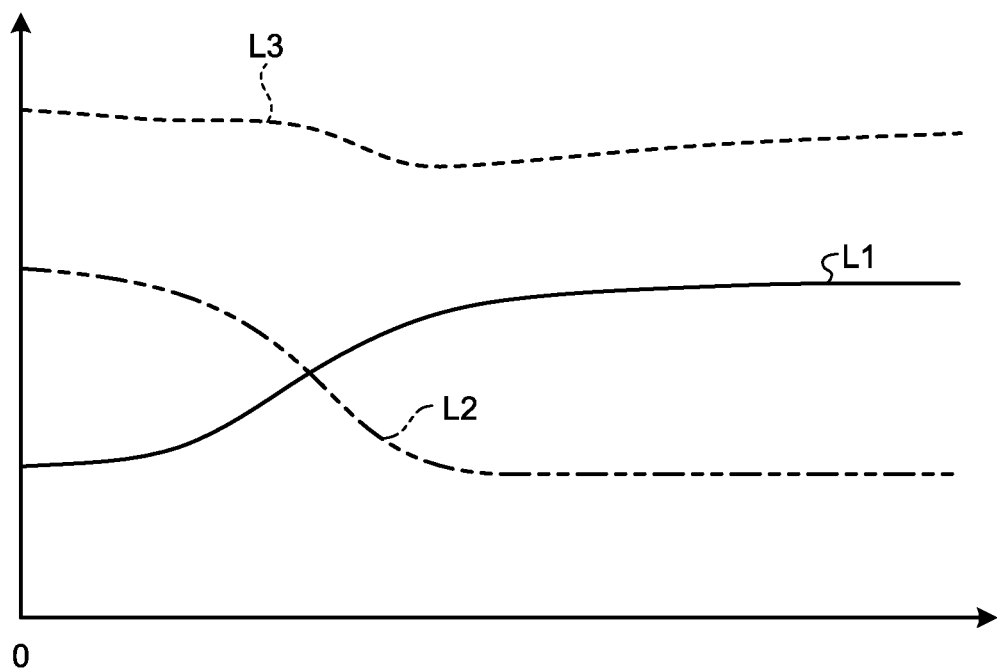
FIG. 8 is a graph illustrating a relationship of voltage-dependent characteristics of an input capacitance of a comparison circuit and an input capacitance of a correction transistor of a correction circuit according to the first embodiment.

Next, voltage-dependent characteristics of the capacitance of the correction transistor 404a and the capacitance of the comparison circuit 403 will be described. FIG. 8 is a graph illustrating the relationship between the voltage-dependent characteristics of the input capacitance of the comparison circuit 403 and the input capacitance of the correction transistor 404a of the correction circuit 404. In FIG. 8, the horizontal axis represents an input voltage (V) of the comparison circuit 403, and the vertical axis indicates a capacitance. In addition, in FIG. 8, a curve L1 indicates a voltage-dependent characteristic of the comparison circuit 403, a curve L2 indicates a voltage-dependent characteristic of the correction transistor 404a, and a curve L3 indicates a voltage-dependent characteristic of a combined capacitance of the capacitance (VB parameter) of the correction transistor 404a and the input capacitance of the comparison circuit 403.

As illustrated in FIG. 8, the correction transistor 404a is set such that the capacitance has the bias voltage dependency of the reverse characteristic to the gate capacitance of the input transistor of the comparison circuit 403. Specifically, a user appropriately sets the bias voltage VB of the correction transistor 404a such that the combined capacitance of the capacitance of the correction transistor 404a and the input capacitance of the comparison circuit 403 is set to be substantially flat. More specifically, as indicated by the curve L2, the user appropriately sets the bias voltage VB of the correction transistor 404a to provide the bias voltage dependency of the reverse characteristic of the gate capacitance of the input transistor of the comparison circuit 403, and thus, can set the combined capacitance of the MOS capacitance of the correction transistor 404a and the input capacitance of the comparison circuit 403 to be substantially flat as indicated by the curve L3.

Figure 9:
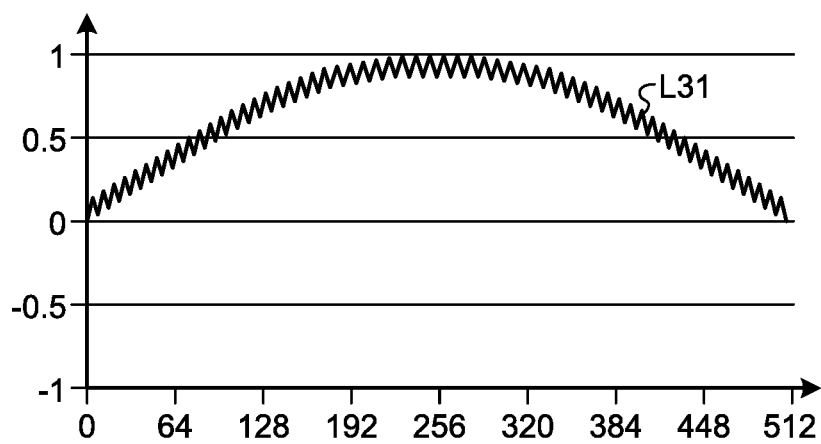
FIG. 9 is a graph illustrating INL characteristics of an output signal output from a conventional successive approximation type A/D conversion device.
Figure 10:
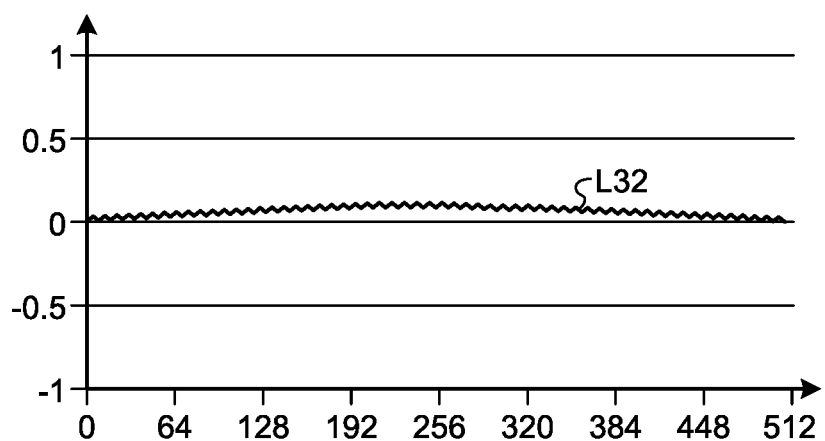
FIG. 10 is a graph illustrating INL characteristics of an output signal output from the first A/D converter according to the first embodiment.

FIG. 9 illustrates an integral non-linearity (INL) characteristic of an output signal output from a conventional successive approximation type A/D conversion device. FIG. 10 illustrates an INL characteristic of an output signal output from the first A/D converter 280. In FIGS. 9 and 10, the horizontal axis represents a code, and the vertical axis represents INL [a.u.]. In addition, a curve L31 in FIG. 9 indicates the INL characteristic of the output signal output from the conventional successive approximation type A/D conversion device, and a curve L32 in FIG. 10 indicates the INL characteristic of the output signal output from the first A/D converter 280.

As indicated by the curve L32 in FIG. 10, the output signal of the first A/D converter 280 is substantially flat, and it is possible to prevent the gain from fluctuating during A/D conversion, and thus, the linearity of the output signal can be maintained.

Operation of Imaging Device

Figure 11A:
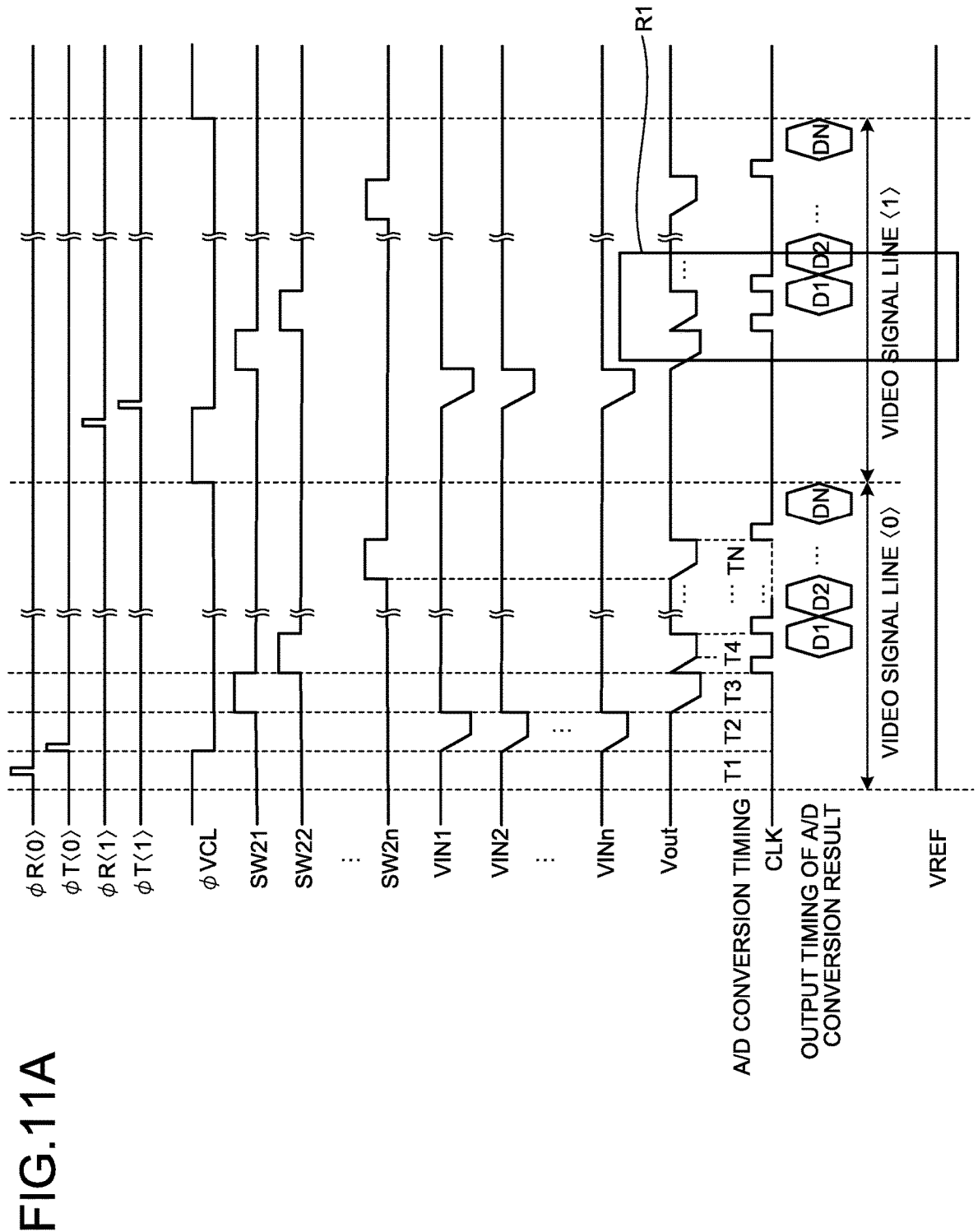
FIG. 11A is a timing chart illustrating an operation of an imaging device according to the first embodiment.
Figure 11B:
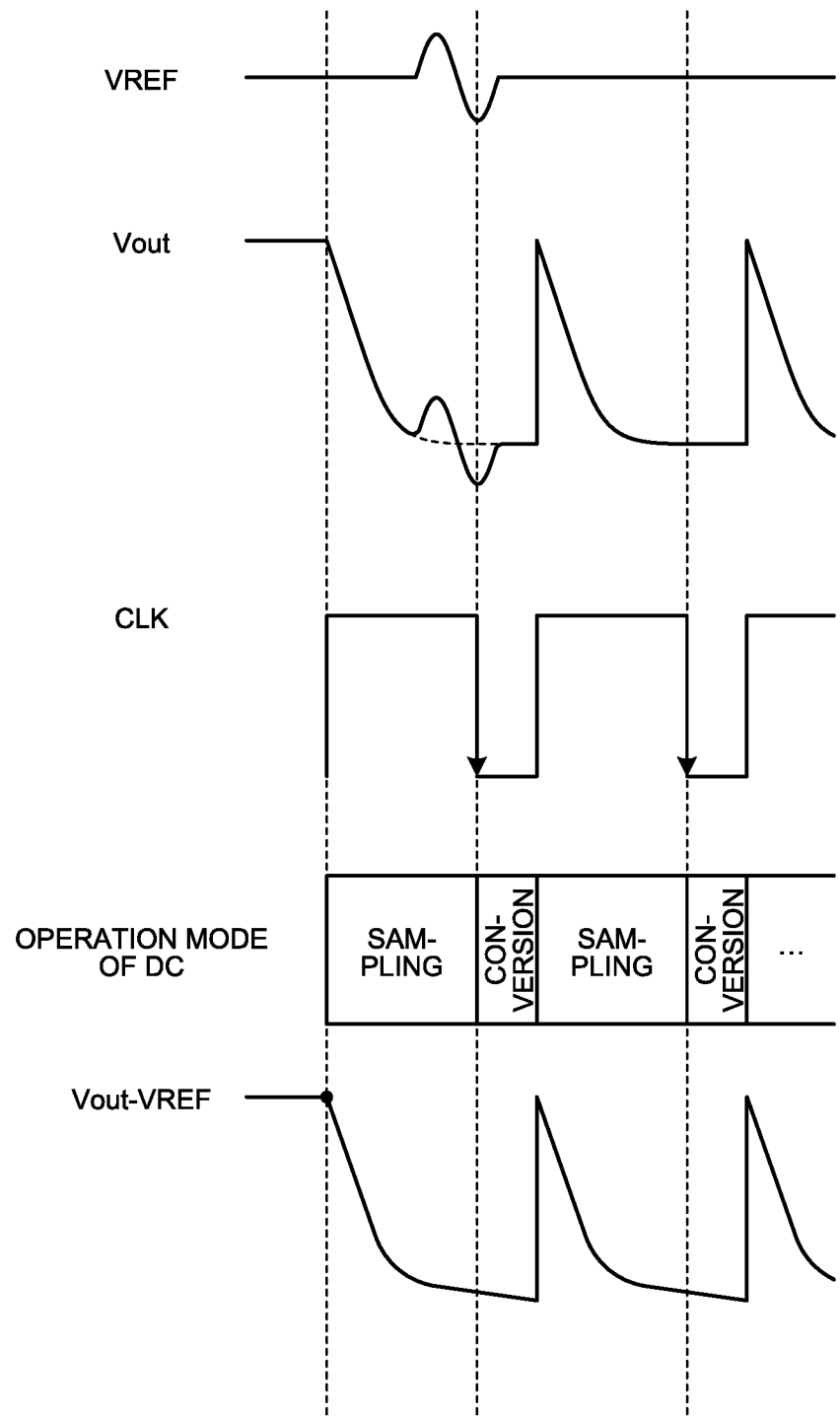
FIG. 11B is a schematic diagram enlarging a part of a timing chart of a region R1 of FIG. 11A.

Next, an operation of the imaging device 20 will be described. FIG. 11A is a timing chart illustrating the operation of the imaging device 20. FIG. 11B is a schematic diagram enlarging a part of a timing chart of a region R1 of FIG. 11A; In FIG. 11A, a description will be given regarding a course of reading an imaging signal from the pixels 230 in a row <n> of the light receiving unit 23 and outputting a digital imaging signal from the A/D conversion device 27. In addition, it is assumed that only the single photoelectric conversion element 231 is included in the pixel 230 in the timing chart illustrated in FIG. 11A for convenience of description. In a case in which the plurality of photoelectric conversion elements 231 are included in the pixel 230 (in the case of pixel sharing), the operation for a single video signal line illustrated in the timing chart is repeatedly performed as many times as the number of the photoelectric conversion elements 231 included in the pixel 230. In addition, FIG. 11A illustrates the drive signal $\phi$R, the drive signal $\phi$T, the drive signal $\phi$VCL, drive signals SW21 to SW2n, voltages VIN1 to VINn of the transfer capacitor 252, an output voltage Vout of the buffer unit 25, a conversion timing of the A/D conversion device 27, a reference clock CLK, an output timing of a conversion result of the A/D conversion device 27, and the reference signal VREF in order from the top. In addition, FIG. 11B illustrates the reference signal VREF, the output voltage Vout of the buffer unit 25, the reference clock CLK, an operation mode of the A/D conversion device 27, and a difference (Vout−VREF) of the reference signal VREF from the output voltage Vout of the buffer unit 25 in order from the top.

As illustrated in FIGS. 11A and 11B, first, the timing generating unit 28 turns on the clamp switch 253 (the drive signal $\phi$VCL is high), turns on the pixel resetting unit 236 (a pulsed drive signal $\phi$R<0> is high), and turns off the transfer transistor 234 (a pulsed drive signal $\phi$T<0> is low) (time T1) such that a noise signal including a specific variation of the pixel 230 serving as a reading target and the noise at the time of pixel resetting is output from the pixel 230 to the vertical transfer line 239. At this time, the clamp switch 253 is kept at the ON-state (the drive signal $\phi$VCL is high) so that the gate of the column source follower buffer 244 is set to a voltage of the clamp voltage VCLP, and the transfer capacitor 252 is charged with VRST−VCLP.

Next, the timing generating unit 28 turns the transfer transistor 234 on (the pulsed drive signal $\phi$T<0> is high) in a state where the clamp switch 253 is turned off (the drive signal $\phi$VCL is low) such that the charge converter 233 reads the signal, photoelectrically converted by the photoelectric conversion element 231, to the vertical transfer line 239 (time T2). In this state, the imaging signal VSIG subjected to the voltage conversion by the charge converter 233 is transferred to the vertical transfer line 239. With this operation, the transfer capacitor 252 is charged with VCLP−(VRST1−VSIG1). As a result, an imaging signal (optical signal) from which the noise signal has been subtracted is output to the gate of the column source follower buffer 244 via the transfer capacitor 252. Here, the signal output to the gate of the column source follower buffer 244 is a signal sampled with reference to the clamp voltage VCLP.

Subsequently, the timing generating unit 28 turns on the column selection switch 255 (the drive signal SW21 is high) (time T3) so that the imaging signal Vout (VCLP−(VRST1−VSIG1)) charged in the transfer capacitor 252 is output to the A/D conversion device 27 via the column source follower buffer 244 and the first global-side circuit 260.

Thereafter, the timing generating unit 28 switches the column selection switch 255 to set the ON state and the OFF state (the drive signal SW21 is low and the drive signal SW22 is high) (time T4) so that the imaging signal Vout (VCLP−(VRST2−VSIG2)) charged in the transfer capacitor 252 is output to the A/D conversion device 27 via the column source follower buffer 244 and the first global-side circuit 260. At this time, the A/D conversion device 27 performs A/D conversion on the imaging signal Vout output from the transfer capacitor 252 based on the reference signal VREF output from the reference signal generating unit 26, and outputs a digital imaging signal D1 to the outside.

Subsequently, the timing generating unit 28 sequentially switches the column selection switch 255 to set the ON state and the OFF state (the drive signals SW22 to SW2n) (time TN) so that the imaging signals Vout (VCLP−(VRSTn−VSIGn)) charged in the transfer capacitor 252 are sequentially output to the A/D conversion device 27 via the column source follower buffer 244 and the first global-side circuit 260. At this time, the A/D conversion device 27 performs A/D conversion on the imaging signals Vout sequentially output from the transfer capacitor 252 based on the reference signal VREF output from the reference signal generating unit 26, and sequentially outputs digital imaging signals D2 to DN to the outside.

As the imaging device 20 repeats such an operation as many times as the number of columns of the light receiving unit 23 (or the number of columns that need to be read), the digital imaging signal in which the fluctuation component of the same phase as the imaging signal has been canceled is output to the outside. Furthermore, the imaging device 20 outputs the digital imaging signal for one frame to the outside by repeating the read operation for one line as many times as the number of pixel rows (or the number of rows that need to be read).

In addition, in-phase noise is added to the reference signal VREF and the imaging signal Vout, but a difference between the output voltage Vout of the buffer unit 25 and the reference signal VREF (Vout−VREF) is not affected by the in-phase noise as illustrated in FIG. 11B. The A/D conversion device 27 samples the imaging signal Vout input from the buffer unit 25 and the reference signal VREF generated from the reference signal generating unit 26 at the same timing, and outputs the digital imaging signal Vout to the outside. As a result, the A/D conversion result is not affected by the in-phase noise.

According to the first embodiment described above, the first global-side circuit 260 is connected with the column source follower buffer 244 (column-side circuit) of the odd-numbered column, sequentially selected by the horizontal scanning unit 245, to form the voltage follower circuit, perform the impedance conversion on the voltage of the imaging signal (Vin) input from the column source follower buffer 244, and output the imaging signal (Vout) amplified by the voltage follower with the amplification factor of one time, and thus, it is possible to use a level of the imaging signal output from the column source follower buffer 244 to the maximum.

In addition, it is possible to secure an input dynamic range and linearity of the A/D conversion device 27 in the case of the output to the A/D conversion device 27 operating at the power-supply voltage lower than that of the pixel 230 according to the first embodiment.

Furthermore, it is possible to reduce input-equivalent noise of the column source follower buffer 244 according to the first embodiment.

In addition, it is possible to convert the imaging signal into the digital imaging signal and output the digital imaging signal without being substantially affected by the in-phase noise since the reference signal generating unit 26 generates the reference signal having the fluctuation component of the same phase as the imaging signal generated by the pixel 230 according to the first embodiment.

In addition, it is possible to prevent the linearity of the output signal output from the A/D conversion device 27 from deteriorating since the capacitance connected to the input terminal of the comparison circuit 403 can be made substantially flat according to the first embodiment.

First Modification of First Embodiment

Next, a first modification of the first embodiment of the disclosure will be described. The first modification of the first embodiment has a configuration different from the reference signal generating unit 26 of the first embodiment described above. Hereinafter, a configuration of a reference signal generating unit according to the first modification of the first embodiment will be described. Incidentally, the same configurations as the endoscopic system 1 according to the first embodiment will be denoted by the same reference signs and the description thereof will be omitted.

Configuration of Reference Signal Generating Unit

Figure 12:
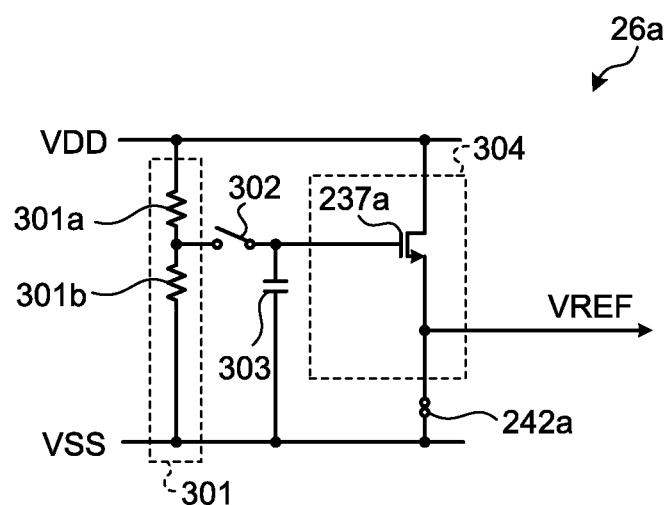
FIG. 12 is a circuit diagram schematically illustrating a configuration of a reference signal generating unit according to a first modification of the first embodiment.

FIG. 12 is a circuit diagram schematically illustrating a configuration of a reference signal generating unit according to a first modification of the first embodiment;

A reference signal generating unit 26a illustrated in FIG. 12 has a configuration in which the noise elimination equivalent circuit 305, the column equivalent circuit 306, and the buffer equivalent circuit 307 are omitted from the reference signal generating unit 26 according to the first embodiment described above, and includes: the resistance dividing circuit 301 formed of the two resistors 301a and 302b; the switch 302 (transistor) driven by a drive signal applied from the timing generating unit 28; a sampling capacitor 303 (capacitor) configured for release from fluctuation independently of the power supply; and the pixel equivalent circuit 304.

According to the first modification of the first embodiment described above, it is possible to generate a reference signal, which has a fluctuation component of the same phase as an imaging signal generated by the pixel 230 and is used for correction processing of the imaging signal, and output the generated reference signal to the A/D conversion device 27, and further, it is possible to reduce the chip area of the imaging element 21.

Second Modification of First Embodiment

A second modification of the first embodiment of the disclosure will be described. The second modification of the first embodiment has a configuration different from the reference signal generating unit 26 according to the first embodiment described above. Hereinafter, a configuration of a reference signal generating unit according to the second modification of the first embodiment will be described. Incidentally, the same configurations as the endoscopic system 1 according to the first embodiment will be denoted by the same reference signs and the description thereof will be omitted.

Configuration of Reference Signal Generating Unit

Figure 13:
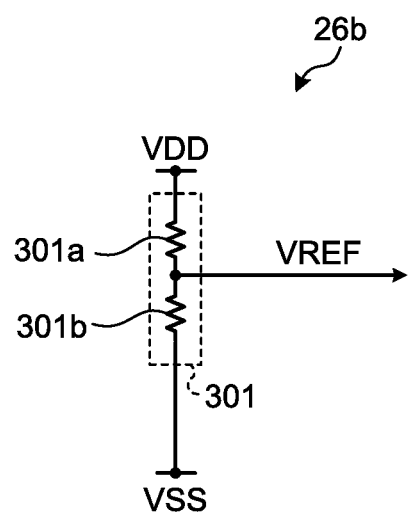
FIG. 13 is a circuit diagram schematically illustrating a configuration of a reference signal generating unit according to a second modification of the first embodiment.

FIG. 13 is a circuit diagram schematically illustrating a configuration of a reference signal generating unit according to a second modification of the first embodiment;

The reference signal generating unit 26b illustrated in FIG. 13 has a configuration in which the switch 302 (transistor), the sampling capacitor 303 (capacitor), the pixel equivalent circuit 304, the noise elimination equivalent circuit 305, the column equivalent circuit 306, and the buffer equivalent circuit 307 are omitted from the reference signal generating unit 26 according to the first embodiment described above, and includes the resistance dividing circuit 301 formed of the two resistors 301a and 301b.

According to the second modification of the first embodiment described above, it is possible to generate a reference signal, which has a fluctuation component of the same phase as an imaging signal generated by the pixel 230 and is used for correction processing of the imaging signal, and output the generated reference signal to the A/D conversion device 27, and further, it is possible to further reduce the chip area of the imaging element 21.

Second Embodiment

Next, a second embodiment will be described. The second embodiment has a configuration different from the imaging element 21 of the first embodiment described above. Hereinafter, a configuration of an imaging element according to the second embodiment will be described, and then, an operation of the imaging element according to the second embodiment will be described. Incidentally, the same configurations as the endoscopic system 1 according to the first embodiment will be denoted by the same reference signs and the description thereof will be omitted.

Configuration of Circuit of Imaging Element

Figure 14:
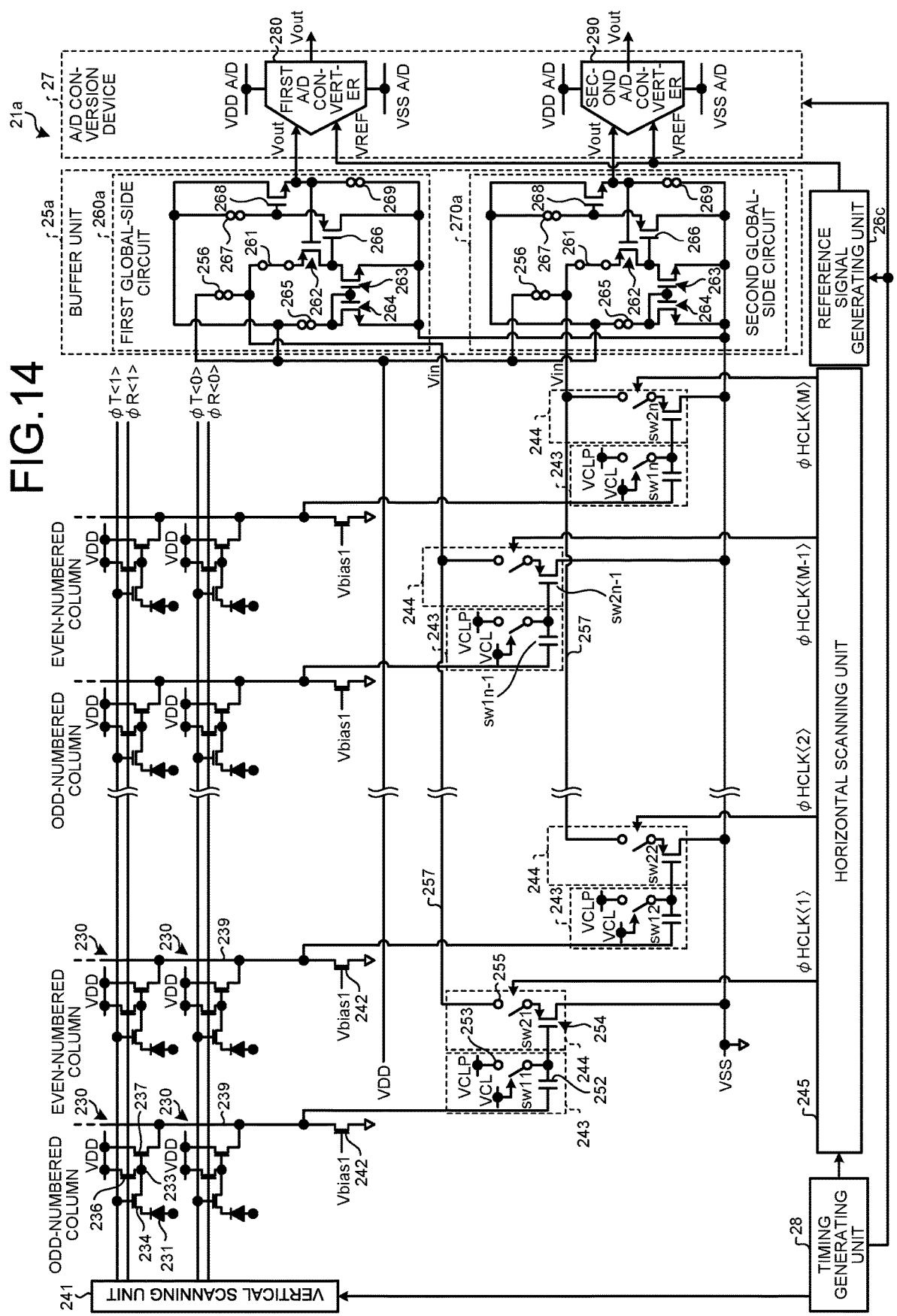
FIG. 14 is a circuit diagram schematically illustrating a configuration of an imaging element according to a second embodiment.

FIG. 14 is a circuit diagram schematically illustrating a configuration of an imaging element according to a second embodiment; An imaging element 21a illustrated in FIG. 14 includes a buffer unit 25a and a reference signal generating unit 26c, instead of the buffer unit 25 and the reference signal generating unit 26 of the imaging element 21 according to the first embodiment described above.

Configuration of Buffer Unit

First, a configuration of the buffer unit 25a will be described. Specifically, the buffer unit 25a is connected with the column source follower buffer 244 sequentially selected by the horizontal scanning unit 245 to form a voltage follower circuit, amplify the input imaging signal by one time with the voltage follower, and output the amplified signal to the A/D conversion device 27. The buffer unit 25a includes a first global-side circuit 260a and a second global-side circuit 270a provided in the odd-numbered column and even-numbered column of the pixel 230, respectively. The first global-side circuit 260a and the second global-side circuit 270a function as impedance converters.

The first global-side circuit 260a further includes a fourth transistor 266, a constant current source 267, a fifth transistor 268, and a constant current source 269, in addition to the configuration of the first global-side circuit 260 according to the first embodiment described above.

The fourth transistor 266 has one end side (source side) connected to the constant current source 267, the other end (drain side) connected to the ground GND, and a gate connected to the column selection switch 255 of the column source follower buffer 244 via the switch 261, the first transistor 262, and the horizontal transfer line 257. The fourth transistor 266 is configured using a PMOS.

The constant current source 267 has one end side connected to the power-supply voltage VDD and the other end side connected to the one end side (source side) of the fourth transistor 266 and a gate of the fifth transistor 268. Incidentally, the constant current source 267 functions as a third constant current source in the second embodiment.

The fifth transistor 268 has one end side (drain side) connected to the power-supply voltage VDD, the other end side (source side) connected to the constant current source 269, and the gate connected to the constant current source 267. The fifth transistor 268 is configured using an NMOS.

The constant current source 269 has one end side connected to the ground GND and the other end side connected to the other end side (source side) of the fifth transistor 268. Incidentally, the constant current source 269 functions as a fourth constant current source in the second embodiment.

The first global-side circuit 260a configured in this manner has a source follower configuration at the output stage, and thus, forms a voltage follower circuit by being connected with the column source follower buffer 244 (column-side circuit) of the odd-numbered column sequentially selected by the horizontal scanning unit 245 to output the imaging signal (Vout) obtained by amplifying the input imaging signal (Vin) by one time with the voltage follower to the A/D conversion device 27.

The second global-side circuit 270a has the same configuration as the above-described first global-side circuit 260a, and includes the constant current source 256, the switch 261, the first transistor 262, the second transistor 263, the third transistor 264, the constant current source 265, the fourth transistor 266, the constant current source 267, the fifth transistor 268, and the constant current source 269.

The second global-side circuit 270a configured in this manner is connected with the column source follower buffer 244 (column-side circuit) of the even-numbered column sequentially selected by the horizontal scanning unit 245 to form a voltage follower circuit and output the imaging signal (Vout) obtained by amplifying the input imaging signal (Vin) by one time using the voltage follower to the A/D conversion device 27.

The reference signal generating unit 26c generates a reference signal, which has a fluctuation component of the same phase as the imaging signal generated by the pixel 230 and is used for correction processing of the imaging signal, and outputs the generated reference signal to the A/D conversion device 27. Incidentally, details of a circuit of the reference signal generating unit 26c will be described later with reference to FIG. 15.

Configuration of Reference Signal Generating Unit

Figure 15:
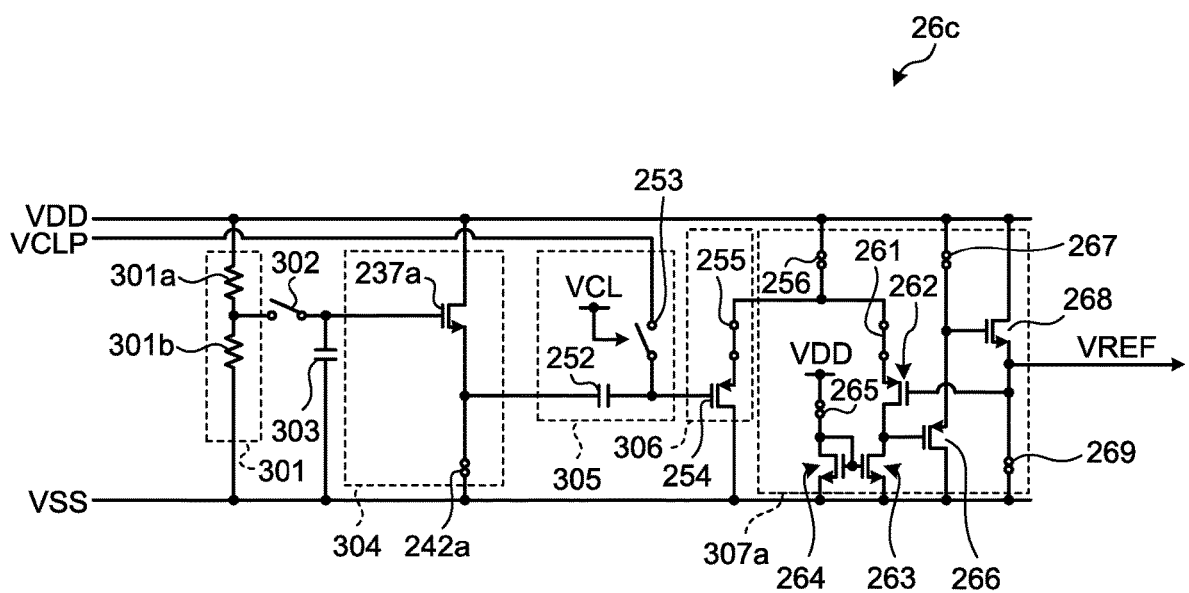
FIG. 15 is a circuit diagram schematically illustrating a configuration of a reference signal generating unit according to the second embodiment.

Next, a detailed configuration of the reference signal generating unit 26c described in FIG. 14 will be described. FIG. 15 is a circuit diagram schematically illustrating the configuration of the reference signal generating unit 26c.

The reference signal generating unit 26c illustrated in FIG. 15 includes a buffer equivalent circuit 307a, instead of the buffer equivalent circuit 307 of the reference signal generating unit 26 according to the first embodiment described above.

The buffer equivalent circuit 307a forms a circuit equivalent to the first global-side circuit 260a, and includes the constant current source 256, the switch 261, the first transistor 262, the second transistor 263, the third transistor 264, the constant current source 265, the fourth transistor 266, the constant current source 267, the fifth transistor 268, and the constant current source 269. Since the buffer equivalent circuit 307a is the circuit equivalent to the above-described first global-side circuit 260a, the detailed description thereof will be omitted.

The reference signal generating unit 26c configured in this manner generates a reference signal (VREF), which has a fluctuation component of the same phase as the imaging signal generated by the pixel 230 and is used for correction processing of the imaging signal, and outputs the generated reference signal (VREF) to the A/D conversion device 27.

Operation of Imaging Device

Figure 16A:
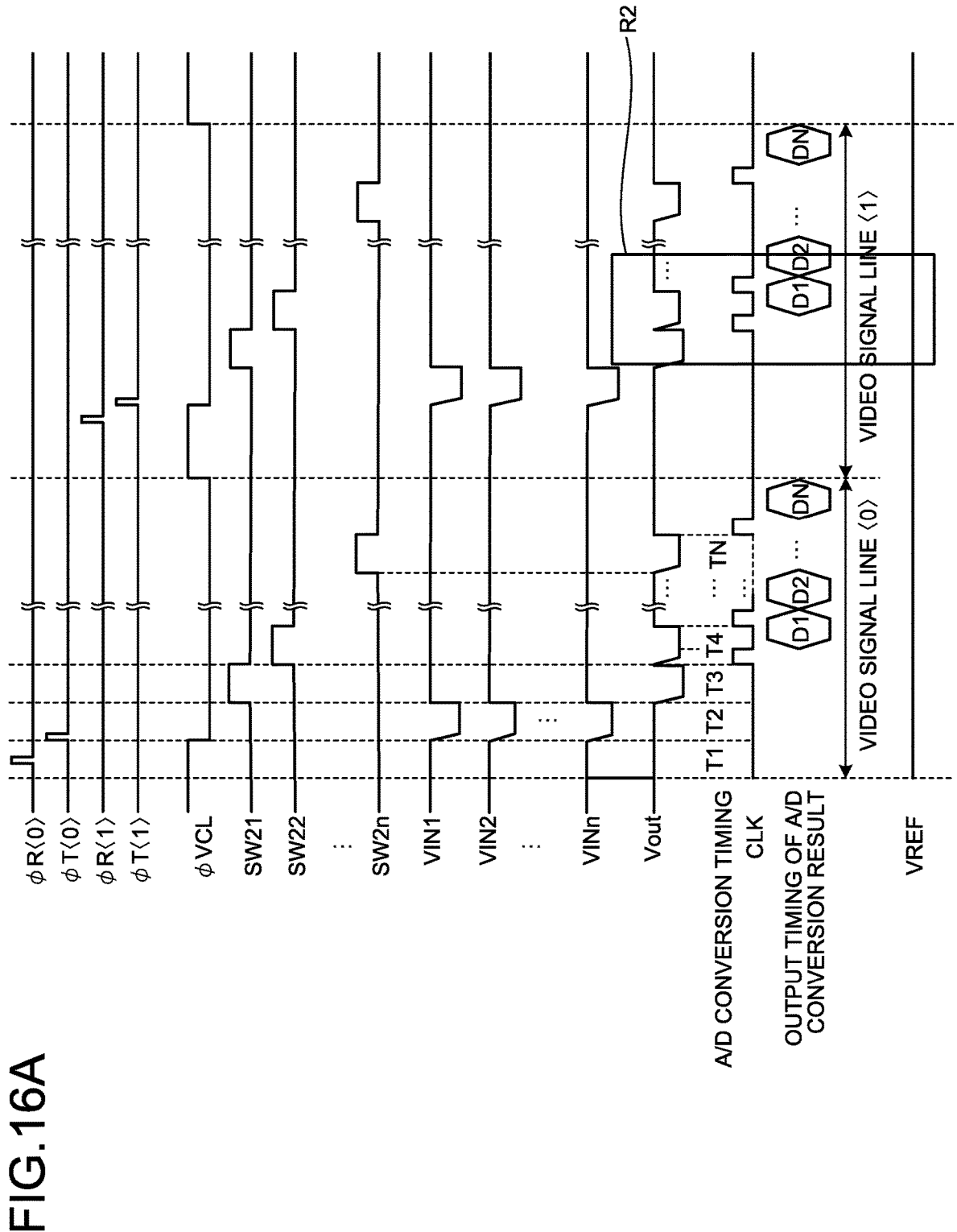
FIG. 16A is a timing chart illustrating an operation of an imaging device according to the second embodiment.

Next, an operation of the imaging device 20 will be described. FIG. 16A is a timing chart illustrating the operation of the imaging device 20. FIG. 16B is a schematic diagram enlarging a part of a timing chart of a region R2 of FIG. 16A; In FIG. 16A, a description will be given regarding a course of reading an imaging signal from the pixels 230 in a row <n> of the light receiving unit 23 and outputting a digital imaging signal from the A/D conversion device 27. In addition, it is assumed that only the single photoelectric conversion element 231 is included in the pixel 230 in the timing chart illustrated in FIG. 16A for convenience of description. In a case in which the plurality of photoelectric conversion elements 231 are included in the pixel 230 (in the case of pixel sharing), the operation for a single video signal line illustrated in the timing chart is repeatedly performed as many times as the number of the photoelectric conversion elements 231 included in the pixel 230. In addition, FIG. 16A illustrates the drive signal φR, the drive signal φT, the drive signal φVCL, the drive signals SW21 to SW2n, the voltages VIN1 to VINn of the transfer capacitor 252, an output voltage Vout of the buffer unit 25a, a conversion timing of the A/D conversion device 27, the reference clock CLK, an output timing of a conversion result of the A/D conversion device 27, and the reference signal VREF in order from the top. In addition, FIG. 16B illustrates the reference signal VREF, the output voltage Vout of the buffer unit 25, the reference clock CLK, an operation mode of the A/D conversion device 27, and a difference (Vout−VREF) of the reference signal VREF from the output voltage Vout of the buffer unit 25 in order from the top.

As illustrated in FIGS. 16A and 16B, first, the timing generating unit 28 turns on the clamp switch 253 (the drive signal φVCL is high), turns on the pixel resetting unit 236 (a pulsed drive signal φR<0> is high), and turns off the transfer transistor 234 (a pulsed drive signal φT<0> is low) (time T1) such that a noise signal including a specific variation of the pixel 230 serving as a reading target and the noise at the time of pixel resetting is output from the pixel 230 to the vertical transfer line 239. At this time, the clamp switch 253 is kept at the ON-state (the drive signal φVCL is high) so that the gate of the column source follower buffer 244 is set to a voltage of the clamp voltage VCLP, and the transfer capacitor 252 is charged with VRST−VCLP.

Next, the timing generating unit 28 turns the transfer transistor 234 φN (the pulsed drive signal φT<0> is high) in a state where the clamp switch 253 is turned OFF (the drive signal φVCL is low) such that the signal, obtained by converting a charge photoelectrically converted by the photoelectric conversion element 231 using the charge converter 233, is read to the vertical transfer line 239 (time T2). In this state, the imaging signal VSIG subjected to the voltage conversion by the charge converter 233 is transferred to the vertical transfer line 239. With this operation, the transfer capacitor 252 is charged with VCLP−(VRST1−VSIG1). As a result, an imaging signal (optical signal) from which the noise signal has been subtracted is output to the gate of the column source follower buffer 244 via the transfer capacitor 252. Here, the signal output to the gate of the column source follower buffer 244 is a signal sampled with reference to the clamp voltage VCLP.

Subsequently, the timing generating unit 28 turns on the column selection switch 255 (the drive signal SW21 is high) (time T3) so that the imaging signal Vout (VCLP−(VRST1−VSIG1)) charged in the transfer capacitor 252 is output to the A/D conversion device 27 via the column source follower buffer 244 and the first global-side circuit 260a.

Thereafter, the timing generating unit 28 switches the column selection switch 255 to set the ON state and the OFF state (the drive signal SW21 is low and the drive signal SW22 is high) (time T4) so that the imaging signal Vout (VCLP−(VRST2−VSIG2)) charged in the transfer capacitor 252 is output to the A/D conversion device 27 via the column source follower buffer 244 and the first global-side circuit 260a. At this time, the A/D conversion device 27 performs A/D conversion on the imaging signal Vout output from the transfer capacitor 252 based on the reference signal VREF output from the reference signal generating unit 26c, and outputs a digital imaging signal D1 to the outside.

Subsequently, the timing generating unit 28 sequentially switches the column selection switch 255 to set the ON state and the OFF state (the drive signals SW22 to SW2n) (time TN) so that the imaging signals Vout (VCLP−(VRSTn−VSIGn)) charged in the transfer capacitor 252 are sequentially output to the A/D conversion device 27 via the column source follower buffer 244 and the first global-side circuit 260a. At this time, the A/D conversion device 27 performs A/D conversion on the imaging signals Vout sequentially output from the transfer capacitor 252 based on the reference signal VREF output from the reference signal generating unit 26c, and sequentially outputs digital imaging signals D2 to DN to the outside.

As the imaging device 20 repeats such an operation as many times as the number of columns of the light receiving unit 23 (or the number of columns that need to be read), the digital imaging signal in which the fluctuation component of the same phase as the imaging signal has been canceled is output to the outside. Furthermore, the imaging device 20 outputs the digital imaging signal for one frame to the outside by repeating the read operation for one line as many times as the number of pixel rows (or the number of rows that need to be read).

In addition, in-phase noise is added to the reference signal VREF and the imaging signal Vout, but a difference between the output voltage Vout of the buffer unit 25 and the reference signal VREF (Vout−VREF) is not affected by the in-phase noise as illustrated in FIG. 16B. The A/D conversion device 27 samples the imaging signal Vout input from the buffer unit 25 and the reference signal VREF generated from the reference signal generating unit 26 at the same timing, and outputs the digital imaging signal Vout to the outside. As a result, the A/D conversion result is not affected by the in-phase noise.

According to the second embodiment described above, the first global-side circuit 260a is connected with the column source follower buffer 244 (column-side circuit) of the odd-numbered column, sequentially selected by the horizontal scanning unit 245, to form the voltage follower circuit, perform the impedance conversion on the voltage of the imaging signal (Vin) input from the column source follower buffer 244, and output the imaging signal (Vout) amplified by the voltage follower with the amplification factor of one time, and thus, it is possible to use a level of the imaging signal output from the column source follower buffer 244 to the maximum.

In addition, it is possible to improve the settling performance of the column source follower buffer 244 since the first global-side circuit 260a is configured as the source follower type according to the second embodiment.

In addition, it is possible to secure the linearity even when the input capacitance of the A/D conversion device 27 is increased since the first global-side circuit 260a is configured as the source follower type according to the second embodiment In addition, it is possible to convert the imaging signal into the digital imaging signal and output the digital imaging signal without being substantially affected by the in-phase noise since the reference signal generating unit 26c generates the reference signal having the fluctuation component of the same phase as the imaging signal generated by the pixel 230 according to the second embodiment.

In addition, it is possible to prevent the linearity of the output signal output from the A/D conversion device 27 from deteriorating since a capacitance connected to an input terminal of the comparison circuit 403 can be made substantially flat according to the second embodiment.

Third Embodiment

Next, a third embodiment will be described. The third embodiment has a configuration different from the first A/D converter 280 and the second A/D converter 290 in the A/D conversion device 27 according to the first embodiment described above. Hereinafter, configurations of a first A/D converter and a second A/D converter according to the third embodiment will be described. Incidentally, the same configurations as the endoscopic system 1 according to the first embodiment will be denoted by the same reference signs and the description thereof will be omitted.

Configuration of First A/D Converter

Figure 17:
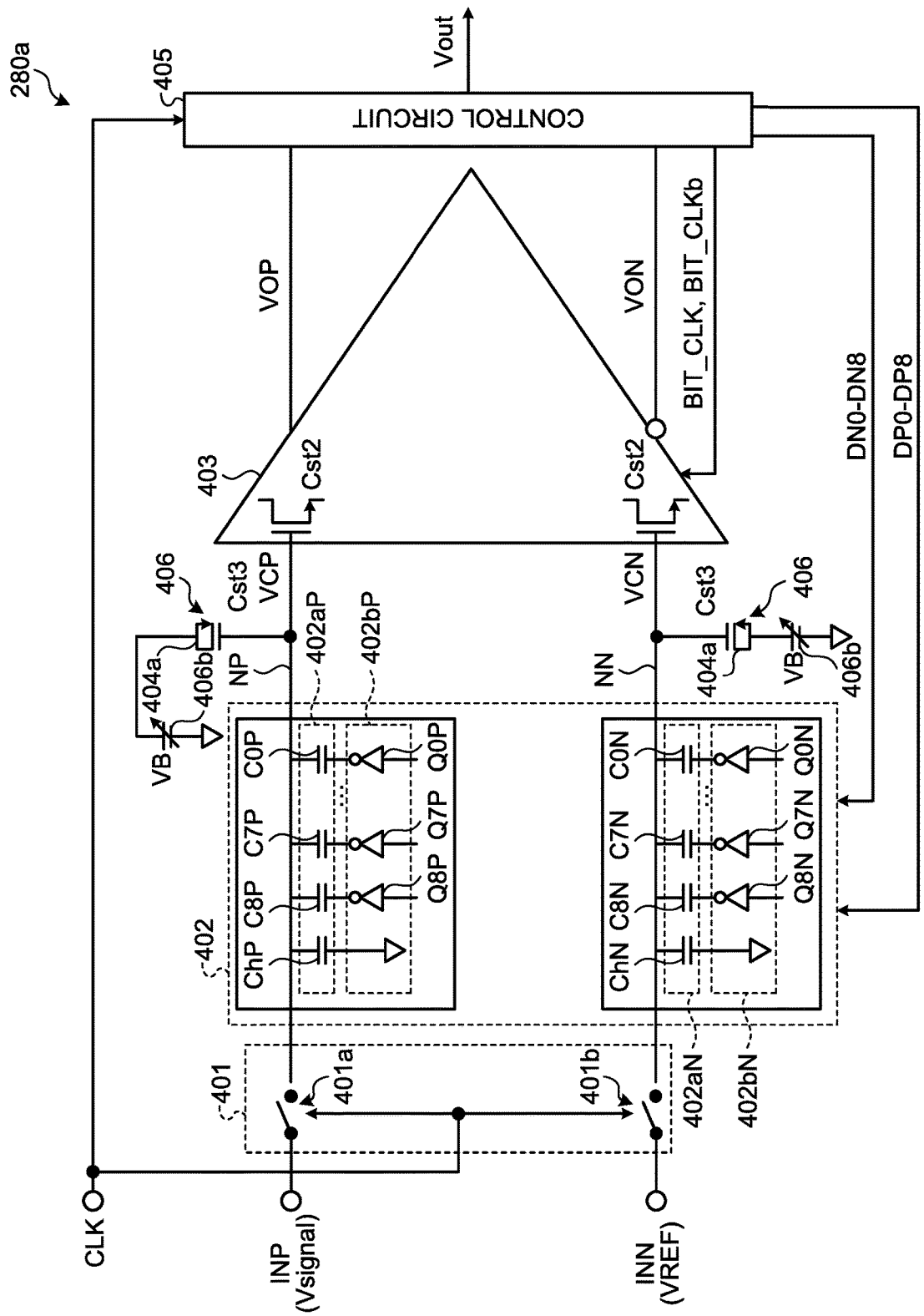
FIG. 17 is a circuit diagram schematically illustrating a configuration of a first A/D converter according to a third embodiment.

FIG. 17 is a circuit diagram schematically illustrating the configuration of the first A/D converter according to the third embodiment. Incidentally, the first A/D converter and the second A/D converter according to the third embodiment have the same circuit configuration, and thus, only the configuration of the first A/D converter will be described hereinafter, and the configuration of the second A/D converter will not be described. In addition, a first A/D converter 280a illustrated in FIG. 17 is a successive approximation type A/D conversion device and is an A/D conversion device with a 9-bit output, but the disclosure is not limited thereto, and the number of output bits can be changed as appropriate.

The first A/D converter 280a illustrated in FIG. 17 includes a correction circuit 406, instead of the correction circuit 404 of the first A/D converter 280 according to the first embodiment described above.

The correction circuit 406 offsets a parasitic capacitance of an input transistor of the comparison circuit 403 to correct a pair of analog signals input to the comparison circuit 403. The correction circuit 406 includes the correction transistor 404a that offsets the parasitic capacitance of the input transistor of the comparison circuit 403, and a bias circuit 406b that applies the bias voltage VB to the correction transistor 404a and is capable of adjusting the bias voltage VB. The bias circuit 406b is configured using, for example, a variable resistor or the like. Incidentally, the bias circuit 406b may be configured using an output signal of a DAC circuit.

Method of Adjusting Bias Voltage VB of Correction Circuit

Figure 18:
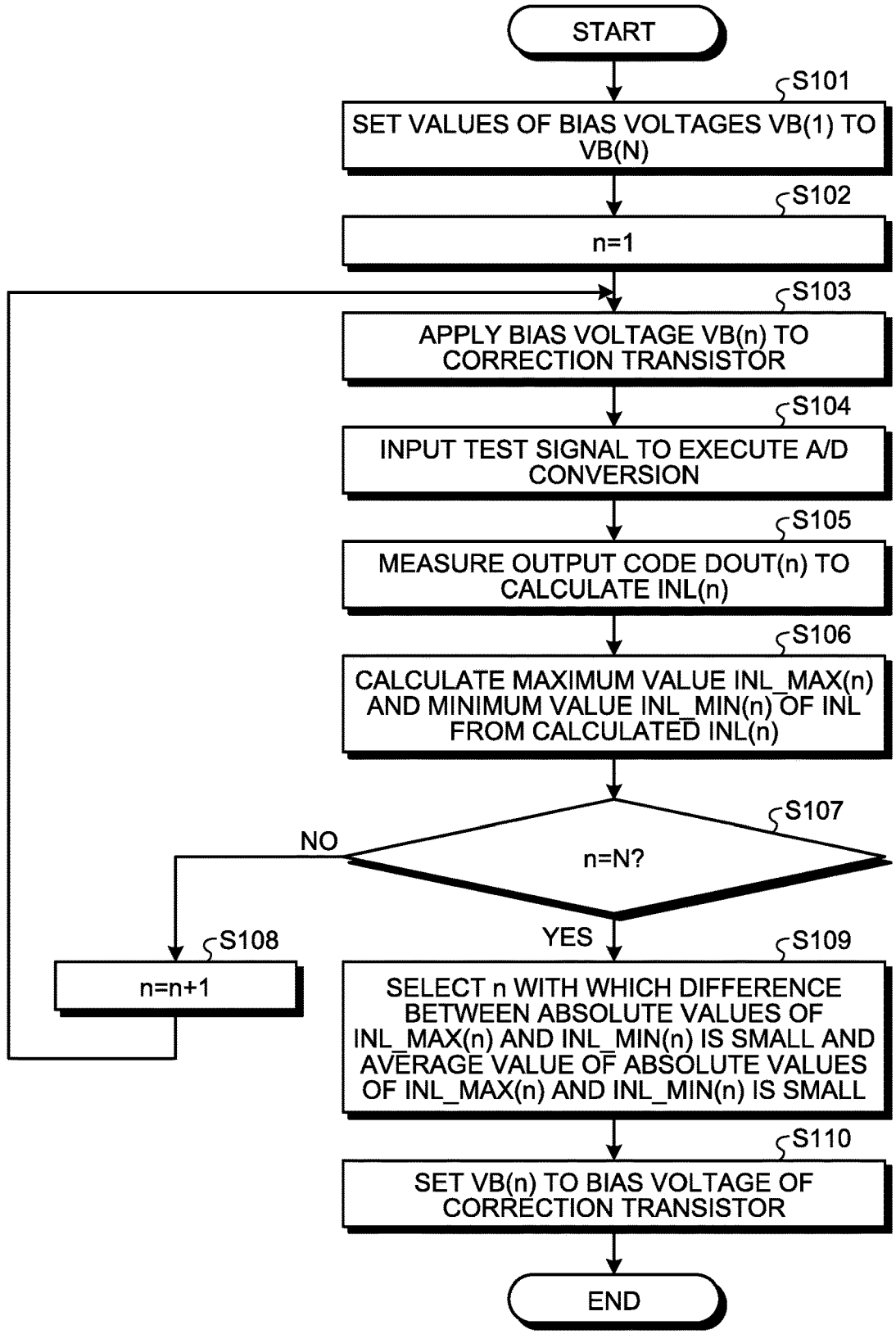
FIG. 18 is a flowchart illustrating a method of adjusting a bias voltage of a correction circuit according to the third embodiment.
Figure 19A:
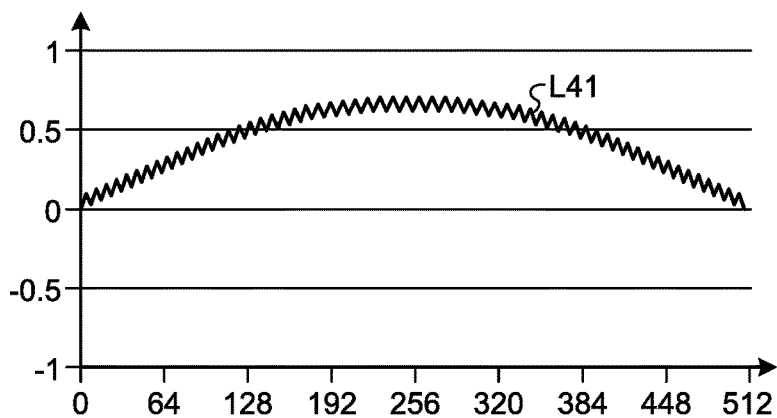
FIG. 19A is a graph schematically illustrating INL characteristics when a bias voltage (1) of the correction circuit according to the third embodiment is changed.
Figure 19B:
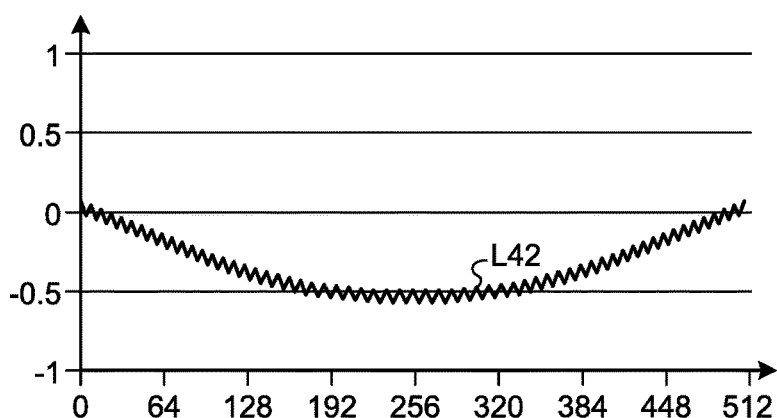
FIG. 19B is a graph schematically illustrating INL characteristics when a bias voltage (N) of the correction circuit according to the third embodiment is changed.
Figure 19C:
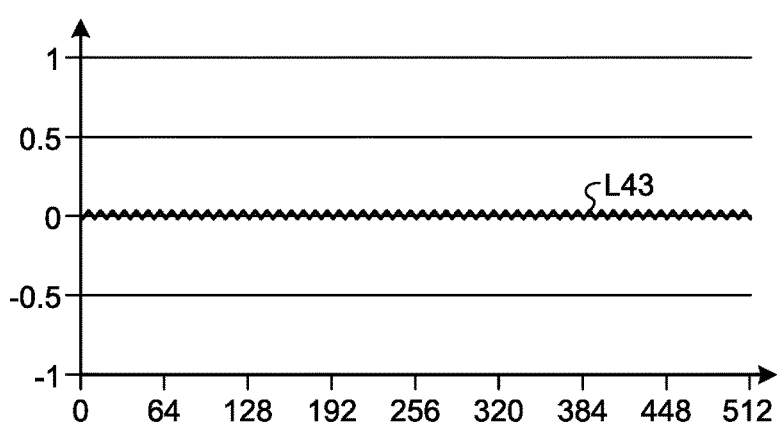
FIG. 19C is a graph schematically illustrating INL characteristics when a bias voltage (n) of the correction circuit according to the third embodiment is changed.

Next, a method of adjusting a bias voltage of the above-described correction circuit 406 will be described. FIG. 18 is a flowchart illustrating the method of adjusting the bias voltage of the correction circuit 406. FIGS. 19A to 19C schematically illustrate INL characteristics (9-bit ADC) when a bias voltage (n) of the correction circuit 406 is changed. In FIGS. 19A to 19C, the horizontal axis represents a code, and the vertical axis represents INL [a.u]. In addition, a curve L41 of FIG. 19A indicates an INL characteristic of a bias voltage VB=VB(1), a curve L42 in FIG. 19B indicates an INL characteristic of a bias voltage VB=Vb(N), and a curve L43 in FIG. 19C indicates an INL characteristic of a bias voltage VB=VB(n).

First, a user adjusts the bias circuit 406b to set values of the bias voltages VB(1) to VB(N) (Step S101), and sets n=1

(Step S102) as illustrated in FIG. 18. Here, N indicates the maximum value at the time of dividing the bias voltage VB.

Subsequently, the bias circuit 406b applies a bias voltage VB(n) to the correction transistor 404a (Step S103).

Thereafter, the user inputs a test signal to the first A/D converter 280a to execute A/D conversion (Step S104), and measures an output code DOUT(n) output from the first A/D converter 280a to calculate INL(n) (Step S105). In this case, an INL characteristic of the bias voltage VB(1) is convex upward as indicated by the curve L41 in FIG. 19A.

Subsequently, the user calculates a maximum value INL_MAX(n) and a minimum value INL_MIN(n) of INL from the calculated INL(n) (Step S106).

Thereafter, the user determines whether n is N (Step S107). When n is N (Step S107: Yes), the process proceeds to Step S109 to be described later.

On the other hand, when n is not N (Step S107: No), the user increments n (n=n+1) (Step S108), and returns to Step S103 and repeats the above-described Steps S103 to S107 until n=N. In this case, an INL characteristic of the bias voltage VB(N) is convex downward as indicated by the curve L42 in FIG. 19B.

In Step S109, the user selects n with which a difference between absolute values of the maximum value INL_MAX(n) and the minimum value INL_MIN(n) is small and an average value of the absolute values of the maximum value INL_MAX(n) and the minimum value INL_MIN(n) is small.

Thereafter, the user sets the bias voltage VB(n) to the bias voltage of the correction transistor 404a (Step S110). Specifically, the user adjusts the bias voltage to be applied from the bias circuit 406b to the correction transistor 404a to be VB(n). In this case, as illustrated in FIG. 19C, an INL characteristic of the bias voltage VB(n) is substantially linear as indicated by the curve L43 in FIG. 19C. After Step S110, the user ends the present process.

According to the third embodiment described above, it is possible to prevent the linearity of the output signal output from the A/D conversion device 27 from deteriorating since a capacitance connected to an input terminal of the comparison circuit 403 can be made substantially flat.

OTHER EMBODIMENTS

The imaging signal generated by the imaging device is transmitted to the processor via the transmission cable in the present disclosure, but is not necessarily transmitted in a wired manner but may be transmitted in a wireless manner. In this case, the imaging signal may be transmitted to the processor according to a predetermined wireless communication standard (for example, Wi-Fi (registered trademark) or Bluetooth (registered trademark)). It is a matter of course that wireless communication may be performed according to other wireless communication standards. Furthermore, not only the imaging signal but also update information for update of various types of information of the endoscope may be transmitted.

In addition, the imaging element is configured in one chip in the present disclosure, but may be configured in two chips by dividing a pixel chip, formed by arranging a plurality of pixels, and a circuit chip, formed by arranging various circuits from the reading unit to the A/D conversion device, and stacking the circuit chip on the pixel chip.

In addition, the digital imaging signal is transmitted from the A/D conversion device to the connector unit via the transmission cable in the present disclosure, but an optical coupler or the like converting a digital imaging signal into an optical signal, for example, may be provided to transmit the digital imaging signal to the connector unit as the optical signal.

In addition, the operation has been described using "first", "next", "subsequently", "thereafter", and the like for the sake of convenience in the description of each operation flowchart described above in the present specification, but these terms do not mean that the operation needs to be implemented in this order.

In addition, the processor and the light source device are integrally formed in the present disclosure, but the disclosure is not limited thereto, and the processor and the light source device may be separate bodies, for example.

In addition, the description has been given by exemplifying the simultaneous endoscope in the present disclosure, but the disclosure can be also applied to a frame-sequential endoscope.

In addition, the disclosure can be also applied to an endoscopic system such as a rigid endoscope, a paranasal sinus endoscope, an electric scalpel, and an inspection probe, in addition to the flexible endoscope (upper and lower endoscopic scopes) in the present disclosure.

In addition, the description has been described by exemplifying the imaging device of the endoscope in which the successive approximation type A/D conversion device is the imaging device and which is provided at the distal end portion of the insertion portion to be inserted into the subject in the present disclosure, but the disclosure is not limited thereto, and can be applied to an imaging device to which a lens device can be freely attached, an imaging device built in a mobile phone, an imaging device without a display monitor, a surveillance camera operated via a network, an imaging device used for a digital camcorder and a microscope, and the like.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging element comprising:
   a plurality of pixels which are arranged in a two-dimensional matrix, each pixel being configured to receive light from an outside and perform photoelectric conversion to generate an imaging signal;
   a noise eliminating circuit which is provided for each of columns in an arrangement of the plurality of pixels, the noise eliminating circuit being configured to eliminate a noise component included in the imaging signal;
   a plurality of column source follower buffers which are provided, respectively, for the columns in the arrangement of the plurality of pixels, each column source follower buffer being configured to amplify the imaging signal from which the noise component has been eliminated by the noise eliminating circuit, and output the amplified signal;
   a horizontal scanning circuit configured to sequentially select the column source follower buffer and output the imaging signal; and
   a buffer circuit which is connected with the column source follower buffer sequentially selected by the horizontal scanning circuit to form a voltage follower circuit, the buffer circuit being configured to perform impedance conversion on a voltage of the imaging signal output from the column source follower buffer, and output the converted signal to the outside, wherein the buffer circuit comprises:
- a first constant current source configured to read the imaging signal from which the noise component has been eliminated by the noise eliminating circuit;
- a first transistor which includes a source terminal connected to the column source follower buffer and a gate terminal connected to a signal line configured to transmit the imaging signal to the outside;
- a second transistor which includes a source terminal connected to ground and a drain terminal connected to a drain terminal of the first transistor and the signal line;
- a third transistor which includes a source terminal connected to the ground; and
- a second constant current source which is connected to a drain terminal of the third transistor, a gate terminal of the third transistor, and a gate terminal of the second transistor.

2. The imaging element according to claim 1, wherein the buffer circuit further comprises:
- a fourth transistor which includes a drain terminal connected to the ground and a gate terminal connected to the column source follower buffer via the first transistor;
- a fifth transistor which includes a drain terminal connected to a power-supply voltage and a source terminal connected to the signal line;
- a third constant current source which includes one end side connected to the power-supply voltage and another end side connected to a source terminal of the fourth transistor and a gate terminal of the fifth transistor; and
- a fourth constant current source which includes one end side connected to the ground and another end side connected to the source terminal of the fifth transistor and the signal line.

3. The imaging element according to claim 1, wherein the column source follower buffer comprises:
- a column source follower transistor configured to amplify the imaging signal from which the noise component has been eliminated by the noise eliminating circuit; and
- a column selection switch configured to switchably connect the column source follower transistor and the buffer circuit, and the buffer circuit further comprises
- a switch which includes an identical resistance value with the column selection switch, the switch being configured to constantly connect the column selection switch and the first transistor.

4. The imaging element according to claim 1, further comprising an A/D conversion circuit configured to perform A/D conversion processing on the imaging signal output from the buffer circuit.

5. The imaging element according to claim 4, further comprising
- a reference signal generating circuit configured to generate a reference signal having a fluctuation component of an identical phase with the imaging signal generated by the pixel,
- wherein the A/D conversion circuit is configured to sample the imaging signal and the reference signal at an identical timing from the outside, and convert the imaging signal into a digital signal.

6. The imaging element according to claim 5, wherein the A/D conversion circuit further comprises:
- a sampling circuit configured to sample the imaging signal and the reference signal as a pair of analog signals input as differential input signals;
- a capacitor circuit which includes a binary capacitance unit holding the pair of analog signals sampled by the sampling circuit, the capacitor circuit being configured to reflect a signal level of a referring signal on the pair of analog signals via the binary capacitance unit to generate a pair of voltage signals;
- a comparison circuit which includes an input transistor to which the pair of voltage signals is input, the comparison circuit being configured to compare one signal forming the pair of voltage signals with another signal forming the pair of voltage signals;
- a correction circuit which is provided on a front side of the comparison circuit, the correction circuit being configured to output the pair of voltage signals whose parasitic capacitances in the input transistor have been offset to the comparison circuit; and
- a control circuit configured to sequentially determine a value of each of bits of a digital signal corresponding to a binary capacitor of the binary capacitance unit by a binary search method, based on a result of the comparison by the comparison circuit, and reflect the value of each of the bits of the digital signal on the referring signal.

7. The imaging element according to claim 5, wherein the reference signal generating circuit includes an element or a circuit having a structure equivalent to the pixel.

8. An imaging device comprising:
- the imaging element according to claim 1; and
- an optical system configured to form a subject image on a light receiving surface of the imaging element.

9. An endoscope comprising:
- the imaging device according to claim 8; and
- an insertion portion which is insertable into a subject and is provided with the imaging device at a distal end portion.

* * * * *